(12) United States Patent
Dow et al.

(10) Patent No.: US 10,888,558 B2
(45) Date of Patent: *Jan. 12, 2021

(54) REGIMENS OF TAFENOQUINE FOR PREVENTION OF MALARIA IN MALARIA-NAIVE SUBJECTS

(71) Applicant: 60 Degrees Pharmaceuticals LLC, Washington, DC (US)

(72) Inventors: Geoffrey S. Dow, Washington, DC (US); Bryan L. Smith, Chevy Chase, MD (US); John P. Jones, Richmond, VA (US); Moshe Shmuklarsky, Bethesda, MD (US); Budda Balasubrahmanyam, Richmond, VA (US)

(73) Assignees: 60 Degrees Pharmaceuticals LLC, Washington, DC (US); The Government Of The United States As Represented By The Secretary Of The Army, Fort Detrick, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/504,533

(22) Filed: Jul. 8, 2019

(65) Prior Publication Data
US 2019/0328723 A1    Oct. 31, 2019

Related U.S. Application Data

(63) Continuation of application No. 15/532,280, filed as application No. PCT/US2015/063425 on Dec. 2, 2015, now Pat. No. 10,342,791.

(60) Provisional application No. 62/086,355, filed on Dec. 2, 2014.

(51) Int. Cl.
*A61K 31/4706* (2006.01)
*C07D 215/40* (2006.01)
*A61P 33/06* (2006.01)

(52) U.S. Cl.
CPC .......... *A61K 31/4706* (2013.01); *A61P 33/06* (2018.01); *C07D 215/40* (2013.01); *Y02A 50/411* (2018.01)

(58) Field of Classification Search
CPC ................................................. A61K 31/4706
See application file for complete search history.

(56) References Cited

U.S. PATENT DOCUMENTS 4,617,394 A    10/1986  Blumbergs et al.
10,342,791 B2 *  7/2019  Smith .................. C07D 215/40

2004/0192724 A1   9/2004  Jain et al.
2012/0101151 A1   4/2012  Gros et al.
2014/0296532 A1  10/2014  Chen et al.

OTHER PUBLICATIONS

Walsh et al., *Randomized Dose-Ranging Study of the Safety and Efficacy of WR 238605 (Tafenoquine) in the Prevention of Relapse of* Plasmodium vivax Malaria *in Thailand*, 4(1) Journal of Infectious Diseases 1282-1287 (Oct. 1999).

(Continued)

*Primary Examiner* — Rei Tsang Shiao
(74) *Attorney, Agent, or Firm* — Panitch Schwarze Belisario & Nadel LLP

(57) ABSTRACT

Methods of prevention of symptomatic malaria in a malaria-naïve, G6PD-normal human subject comprising administering to the human subject a compound of Formula (I), a pharmaceutically acceptable salt thereof, or pharmaceutical composition comprising a compound of Formula (I). A compound of Formula (I) can be administered prior to potential exposure of a species of *Plasmodium*, during potential exposure of a species of *Plasmodium*, and after potential exposure of a species of *Plasmodium*. The methods of the invention also pertains to kits comprising specific doses of Formula (I), a pharmaceutically acceptable salt thereof, or pharmaceutical composition comprising a compound of Formula (I), and instructions for administration of dosing quantity and frequency. The methods of the invention also pertain to determining doses of Formula (I) that meet the general regulatory requirement for a drug to be efficacious in the prevention of malaria in malaria-naïve subjects. The methods of the invention further pertain to using the described algorithm to derive dosing regimens which can provide protection against symptomatic malaria in malaria-naïve, G6PD-normal subjects.

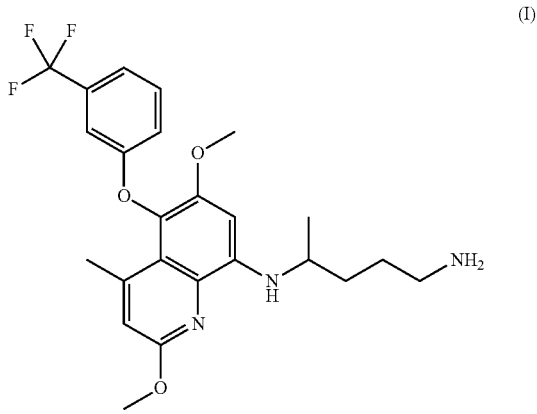

(I)

33 Claims, 9 Drawing Sheets

(56) References Cited

OTHER PUBLICATIONS

Nasveld et al., *Treatment of acute vivax malaria with tafenoquine*, 99 Transactions of the Royal Society of Tropical Medicine and Hygiene, 2-5 (2005).
Shanks et al., *A New Primaquine Analogue, Tafenoquine (WR 238605), for Prophylaxis against* Plasmodium falciparum *Malaria*, 33 Clinical Infectious Diseases 1968-1974 (2001).
Crockett et al., *Teafenoquine: a promising new antimalarial agent*, 16(5) Expert Opin. Investig. Drugs 705-715 (2007).
Supplementary European Search Report issued in related EP Patent Application No. 15 86 5264, dated on Apr. 20, 2018.
Nasveld et al., *Comparison of tafenoquine (WR238605) and primaquine in the post-exposure (terminal) prophylaxis of vivax malaria in Australian Defence Force personnel*, 96 Transactions of the Royal Society of Tropical Medicine and Hygiene 683-684 (2002).
Andersen et al., *Successful double-blinded, randomized, placebo-controlled filed trial of azithromycin and doxycycline as prophylaxis for malaria in western Kenya*, 26(1) Clin. Infect. Dis. 146-150 (1998) (abstract only).
Arguin et al., *Malaria*, Centers for Disease Control and Prevention, Chapter 3 Infectious Disease Related to Travel (2018).
Bhuyan et al., *Stimulation of Suicidal Erythrocyte Death by Tafenoquine*, 39 Cellular Physiology and Biochemistry 2464-2476 (2016).
Brueckner et al., *Prophylaxis of* Plasmodium falciparum *Infection in a Human Challenge Model with WR 238605, a New 8-Aminoquinoline Antimalarial*, 42(5) Antimicrobial Agents and Chemotherapy 1293-1294 (May 1998).
Baird et al., *Short Report: Therapeutic Efficacy of Chloroquine Combined with Primaquine Against* Plasmodium Falciparum *in Northeastern Papua, Indonesia*, 66(6) Am. J. Tro. Med. Hyg. 659-660 (2002).
Deye et al., *Primaquine for Prophylaxis of Malaria: Has the CYP Sailed?*, 21 J. Travel Med. 67-69 (2014).
Taylor et al., *Malaria prophylaxis using azithromycin: a double-blind, placebo-controlled trial in Iran Jaya, Indonesia*, 28(1) Clin. Infec. Dis. 74-81 (1999) (abstract only).
*US Food and Drug Administration Approves ARAKODA™ (tafenoquine) tables for oral use; First preventative antimalarial approve in almost two decades*, Press Release from 60 Degrees Pharma (Aug. 9, 2018).
Dow et al., *A restrospective analysis of the protective efficacy of tafenoquine and mefloquine as prophylactic anti-malarials in non-immune individuals during deplyoment to a malaria-endemic area*, 13(49) Malaria Journal 1-13 (Feb. 6, 2014).
Edstein et al., *Gender differences in gastrointestinal disturbances and plasma concentrations of tafenoquine in healthy volunteers after tafenoquine administration for post-exposure vivax malaria prophylaxis*, 101 Transactions of the Royal Society of Tropical Medicine and Hygiene 226-230 (2007).

\* cited by examiner

REGIMENS OF TAFENOQUINE FOR PREVENTION OF MALARIA IN MALARIA-NAIVE SUBJECTS

CROSS-REFERENCE TO RELATED APPLICATIONS

This application is a Continuation application of U.S. patent application Ser. No. 15/532,280, filed on Jun. 1, 2017, now U.S. Pat. No. 10,342,791, issued on Jul. 9, 2019, which is a U.S. National Stage Application pursuant to 35 U.S.C. § 371 of International Patent Application PCT/US2015/063425, filed on Dec. 2, 2015, and published as WO 2016/089995 on Jun. 9, 2016, which claims priority to U.S. Provisional Patent Application 62/086,355, filed on Dec. 2, 2014, all of which are incorporated herein by reference in their entireties for all purposes.

BACKGROUND OF THE INVENTION

There are 217,000,000 cases of malaria and 627,000 deaths annually in tropical countries (http://www.who.int/gho/malaria/epidemic/en/). The disease is caused by five species of Plasmodium: P. vivax, P. falciparum, P. ovale, P. knowlsi, and P. malariae, all protozoan parasites transmitted by mosquitoes. The symptoms of malaria are caused by the amplification of the parasite in red blood cells, after an initial cycle of replication in the liver. Individuals who reside in areas of heavy malaria transmission develop a partial immunity to the disease after repeated exposure to the parasites which prevents the development of symptoms in response to new infection. Travelers from temperate countries, who have not been exposed to malaria, are termed 'non-immune individuals' or 'malaria-naïve,' are at high risk of severe clinical disease and death if they contract malaria during a visit to a tropical country. These individuals, to prevent malaria, are often administered a course of 'prophylactic' antimalarial drugs (e.g., mefloquine, chloroquine, doxycycline, primaquine, or atovaquone-proguanil) that maintain a minimum protective level of active drug in their blood during travel. Upon return, these individuals must take a 14-day course of primaquine to kill the latent stages of P. vivax and P. ovale and/or continue to maintain active blood levels of drug to suppress any remaining viable blood stage parasites of all species.

An appropriate prophylactic antimalarial drug, dosed in a manner to maintain therapeutic levels indefinitely, could protect a non-immune individual from contracting symptomatic malaria, caused by any human species of Plasmodia, during the period of exposure to malaria vectors if it killed (i) 100% of developing liver schizonts upon entry into the liver after a mosquito bite, or (ii) 100% of merozoites upon their entry from the liver into the blood stream. In the special case of relapsing malaria parasites such as P. vivax and P. ovale, a hypothetical malaria drug would have to exhibit any of the aforementioned inhibitory properties, plus, in addition, kill developing liver schizonts after the activation of latent hypnozoites. However, in order to maintain high levels of clinical protective efficacy, 100% killing of merozoites emerging from the liver is an absolute requirement if a drug does not kill 100% of developing liver schizonts (originating from either sporozoites or hypnozoites).

Tafenoquine is an 8-aminoquinoline analog of primaquine, the approved drug that is primarily used to eliminate the latent liver stages of P. vivax (Shanks and Edstein 2005). Tafenoquine is known to exhibit a potent inhibitory effect on developing liver schizonts. Tafenoquine is generally presumed to also exhibit antihypnocytocidal effects against P. vivax. The inhibitory effect of tafenoquine on asexual blood stage parasites is also known. The drug is active against the blood stages of P. falciparum in vitro, P. berghei in mice in vivo, and cured both chloroquine sensitive and resistant P. vivax infections in Aotus monkeys. Tafenoquine is being developed for the complete, also known as radical, cure of P. vivax malaria, and for the chemoprophylaxis (i.e., prevention) of malaria in malaria-naïve travelers. Structural features installed to block metabolic sites on the core 8-aminoquinoline scaffold provide the drug with an extremely long half-life (weeks) relative to primaquine (hours). Tafenoquine's long half-life makes it suitable for weekly administration, making it an ideal replacement for other weekly drugs such as chloroquine (limited efficacy due to resistance) and mefloquine (no longer commonly prescribed due to its association with adverse neurologic effects). The capacity for weekly administration (better compliance) and utility against the dormant, hypnozoites of P. vivax (14-day treatment with primaquine not required) confer superior utility to tafenoquine relative to daily prophylactic drugs such as doxycycline and atovaquone-proguanil.

Glucose-6-phosphate dehydrogenase deficiency (G6PD deficiency) is characterized by abnormally low levels of G6PD, due to an X-linked recessive genetic deficiency and is the most common human enzyme defect. G6PD is a metabolic enzyme involved in the pentose phosphate pathway and is especially important in red blood cell metabolism (Frank 2005). G6PD-deficient individuals may exhibit hemolytic anemia in response to a number of causes, most commonly infection or exposure to certain medications or fava beans. Individuals that are carriers of the G6PD allele appear to be protected to some extent against malaria. Further, in some cases dominant males have shown complete immunity to the disease. This accounts for the persistence of the allele in certain populations in that it confers a selective evolutionary survival advantage (Lewis, Ricki).

Many substances are potentially harmful to people with G6PD deficiency. Variation in response to these substances makes individual predictions difficult. Such harmful substances include antimalarial drugs which can cause acute hemolysis in people with G6PD deficiency. These drugs include primaquine, pamaquine, and chloroquine. There is evidence that other antimalarials may also exacerbate G6PD deficiency, but only at higher doses. Sulfonamides (such as sulfanilamide, sulfamethoxazole, and mafenide), thiazolesulfone, methylene blue, and naphthalene should also be avoided by people with G6PD deficiency as they antagonize folate synthesis, as should certain analgesics (such as aspirin, phenazopyridine, and acetanilide) and several non-sulfa antibiotics (nalidixic acid, nitrofurantoin, isoniazid, dapsone, and furazolidone) (Frank J E; Warrel, David A.; and Beutler, E.). Henna has been known to cause haemolytic crisis in G6PD-deficient infants (Raupp P, et al.).

Tafenoquine, like other 8-aminoquinolines, may cause hemolytic anemia in individuals with G6PD deficiency; such anemia is dose-related. For this reason, tafenoquine can be more readily given to individuals shown to have normal levels of G6PD in their blood. Although in theory this can be accomplished through the use of one of at least 30 commercial test kits available, the gold standard for the diagnosis of G6PD deficiency is to use a direct, quantitative enzymatic assay to establish the amount of G6PD in the blood (von Seidlein, et al.). This test is usually administered as a screening test prior to travel or deployment by travel doctors, public health or military medical personnel, as a routine component of a pre-travel check list. Best practice is to perform double screening to reduce the likelihood of false negative results.

None of the prior regimens of tafenoquine described in the literature provide the optimal balance between tolerability and achieving a sufficiently high steady state minimum concentration of tafenoquine above a threshold of therapeutic efficacy to prevent symptomatic malaria in malaria-naïve, normal Glucose-6-phosphate dehydrogenase (G6PD) individuals. The present invention satisfies this long-felt need by specifying a set of dosing regimens which achieve the minimum concentration required to achieve protection from development of symptomatic malaria in malaria-naïve individuals while minimizing adverse events.

Furthermore, the present invention specifies dosing regimens in which the overall exposure to tafenoquine may not change, but the maximum steady state concentrations will be reduced, and the minimum steady state concentrations will be increased to ensure therapeutic efficacy by more frequent tafenoquine dosing.

Further, there are no available antimalarial drugs that work everywhere in the world, can be administered once weekly, and have activity against the latent liver stages of *P. vivax*. The Applicants' invention directly addresses all of these therapeutic needs and also does so with one drug—tafenoquine.

Post-exposure prophylaxis is currently achieved using a combination of daily primaquine plus a blood schizonticidal drug like doxycycline or mefloquine. Tafenoquine fulfills all these tasks in monotherapy doses administered once daily to once weekly following a potential exposure to a *Plasmodium* species. In some aspects, tafenoquine can provide post-exposure prophylactic protection by relying on higher dosing during potential exposure and the relatively long half-life of the drug to ensure protective levels of tafenoquine are maintained for at least three weeks after returning from a malarious area.

SUMMARY OF THE INVENTION

The present invention pertains to novel dosing regimens for tafenoquine for malaria prophylaxis. In some embodiments, the regimens are administered to malaria-naïve subjects. In other embodiments, the subjects are Glucose-6-phosphate dehydrogenase (G6PD) normal human subjects. The present invention pertains to prophylaxis and post-exposure prophylaxis against malaria of all species. The present invention also pertains to methods for determining doses of tafenoquine that meet the Food and Drugs Administration (FDA) and other non US-based regulatory authorities' general regulatory requirement for a malaria prophylactic drug to be 95% effective in the prevention of symptomatic malaria in malaria-naïve, Glucose-6-phosphate dehydrogenase (G6PD) normal human subjects. The present invention describes dosing regimens which can provide protection against symptomatic malaria under various scenarios in groups of people within certain age range and body weight ranges.

In one aspect, the method of prevention of malaria in a human subject comprises administering to the human subject an initial dose of a compound of Formula (I), a pharmaceutically acceptable salt thereof, or a pharmaceutical composition comprising a compound of Formula (I), wherein said initial dose comprises one or more doses, e.g., at least once per day for three days, prior to potential exposure of at least one species of *Plasmodium*; followed by administering to the human subject an exposure dose of a compound of Formula (I), a pharmaceutically acceptable salt thereof, or a pharmaceutical composition comprising a compound of Formula (I), one or more times per week, during potential exposure of at least one species of *Plasmodium*, e.g., once per day, once every two to six days, or once per week; followed by administering to the human subject a post-exposure dose of a compound of Formula (I), a pharmaceutically acceptable salt thereof, or a pharmaceutical composition comprising a compound of Formula (I), one or more times, for example at least once per day for three days, once per week for three weeks, or at least three times, after potential exposure of at least one species of *Plasmodium*, and, wherein a serum or plasma concentration of at least 80 ng/mL of a compound of Formula (I) is attained prior to potential exposure, maintained during potential exposure, and maintained for at least three weeks after potential exposure to at least one species of *Plasmodium*, and wherein the human subject is malaria-naïve and Glucose-6-phosphate dehydrogenase (G6PD) normal, and wherein Formula (I) has the following structure,

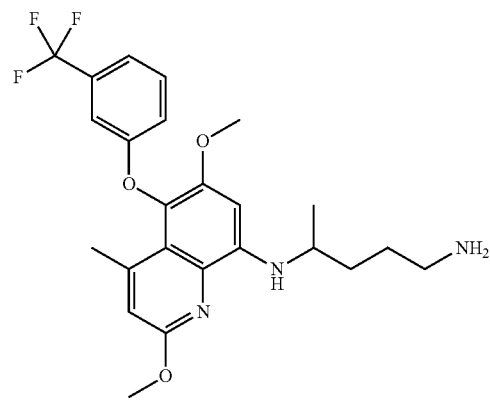 [SMILES: COc1cc(C)c2c(Oc3cccc(C(F)(F)F)c3)c(OC)cc(NC(C)CCCN)c2n1]

An alternative name for the compound of Formula (I) is -[2,6-Dimethoxy-4-methyl-5-[3-(trifluoromethyl)phenoxy]quinolin-8-yl]pentane-1,4-diamine, or a pharmaceutical acceptable salt thereof. Formula (I) may also have the following related structure,

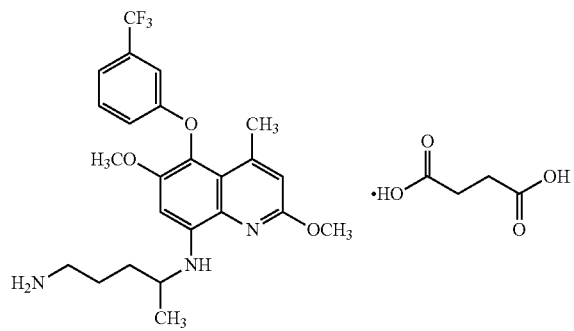

The chemical Abstract Service (CAS) number for above identified succinate salt structure is 106635-81-8.

In another aspect, the present invention pertains to a method of prevention of post-exposure malaria in a human subject, comprising administering to the human subject a primary dose of a compound of Formula (I), a pharmaceutically acceptable salt thereof, or a pharmaceutical composition comprising a compound of Formula (I); and administering to the human subject a post-exposure dose of a compound of Formula (I), a pharmaceutically acceptable salt thereof, or a pharmaceutical composition comprising a compound of Formula (I), after administration of said primary dose and after potential exposure to at least one species of *Plasmodium*, wherein said primary dose comprises one or more individual doses sufficient to achieve a serum or plasma concentration of at least about 80 ng/mL of a compound of Formula (I), and wherein said post-exposure dose comprises one or more individual doses sufficient to maintain for at least three weeks after potential exposure of at least one species of *Plasmodium*, a serum or plasma concentration of at least about 80 ng/mL of a compound of Formula (I), wherein the human subject is malaria-naïve and G6PD normal, and wherein Formula (I) has the following structure,

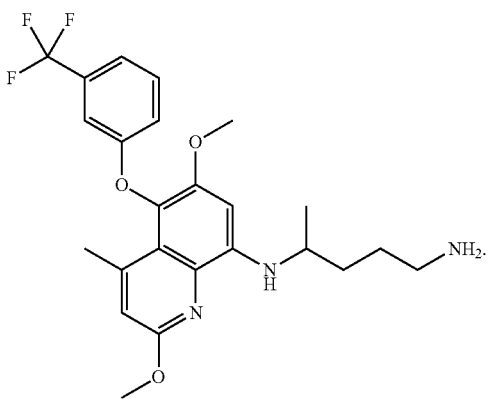 [SMILES: COc1cc(C)c2c(Oc3cccc(C(F)(F)F)c3)c(OC)cc(NC(C)CCCN)c2n1]

In another aspect, the invention pertains to a method of prevention of malaria in a human subject, comprising administering to the human subject an initial dose of a compound of Formula (I), a pharmaceutically acceptable salt thereof, or a pharmaceutical composition comprising a compound of Formula (I), one or more times prior to potential exposure of at least one species of *Plasmodium*, wherein each said initial dose is between about 75 and about 299 mg; and administering to the human subject an exposure dose of a compound of Formula (I), a pharmaceutically acceptable salt thereof, or a pharmaceutical composition comprising a compound of Formula (I), one or more times per week during potential exposure of at least one species of *Plasmodium*, wherein the total administered amount of the exposure dose is between about 175 and 195 mg per week, and wherein the human subject is malaria-naïve and G6PD normal, and wherein Formula (I) has the following structure,

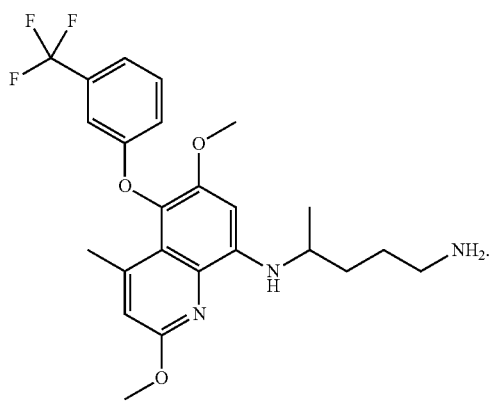

The invention also pertains to kits for carrying out the methods described herein. In one specific embodiment, the kit comprises one or more initial dose(s) of about 40 to about 299 mg of a compound of Formula (I), a pharmaceutically acceptable salt thereof, or a pharmaceutical composition comprising a compound of Formula (I); multiple exposure doses wherein the total administered amount of exposure dose is about 75 to about 299 mg per week of a compound of Formula (I), a pharmaceutically acceptable salt thereof, or a pharmaceutical composition comprising a compound of Formula (I); one or more post-exposure dose(s) of about 40 to about 299 mg of a compound of Formula (I), a pharmaceutically acceptable salt thereof, or a pharmaceutical composition comprising a compound of Formula (I); and instructions for taking said initial dose(s) one or more times prior to potential exposure of at least one species of *Plasmodium*, and taking said exposure dose one or more times per week, for example once per day, once every two to six days, or once per week, during potential exposure of at least one species of *Plasmodium*, and for taking said post-exposure dose(s) one or more times after potential exposure of at least one species of *Plasmodium*, and wherein Formula (I) has the following structure,

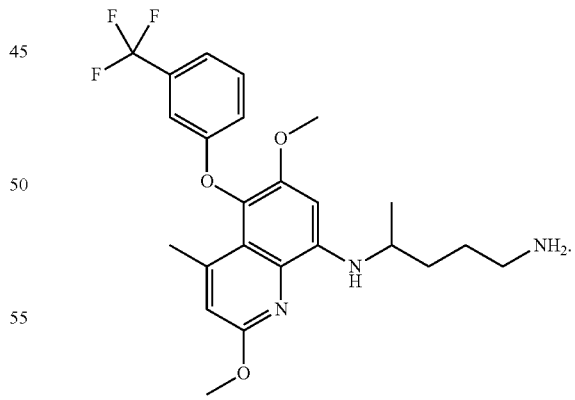

In another embodiment, the invention pertains to a kit comprising one or more initial doses of a compound of Formula (I), a pharmaceutically acceptable salt thereof, or a pharmaceutical composition comprising a compound of Formula (I), wherein the total combined amount of the compound of Formula (I) in all pre-exposure doses exceeds about 500 mg; and a plurality of exposure doses of a compound of Formula (I), a pharmaceutically acceptable salt thereof, or a pharmaceutical composition comprising a compound of Formula (I), wherein the total weekly amount of the compound of Formula (I) is at least about 175 mg per week; and instructions for taking said initial dose(s) one or more times prior to potential exposure of at least one species of *Plasmodium*, and taking said exposure dose two or more times per week, wherein Formula (I) has the following structure,

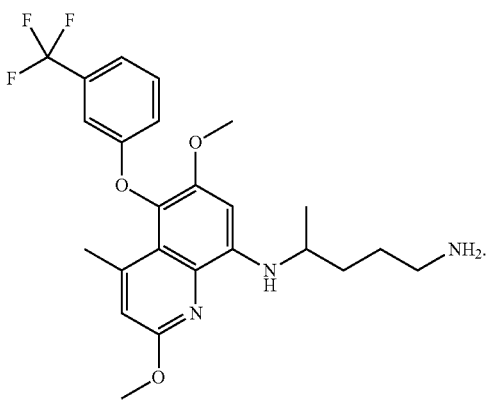

The invention also pertains to a kit comprising one or more primary dose(s) of about 40 to about 299 mg of a compound of Formula (I), a pharmaceutically acceptable salt thereof, or a pharmaceutical composition comprising a compound of Formula (I); one or more post-exposure dose(s) of about 40 to about 299 mg of a compound of Formula (I), a pharmaceutically acceptable salt thereof, or a pharmaceutical composition comprising a compound of Formula (I); and instructions for taking said primary dose(s) one or more times prior to taking said post-exposure dose(s) one or more times, for example at least once per day for three days, once per week for one to three weeks, three times, or at least three times after potential exposure of at least one species of *Plasmodium*, and wherein Formula (I) has the following structure,

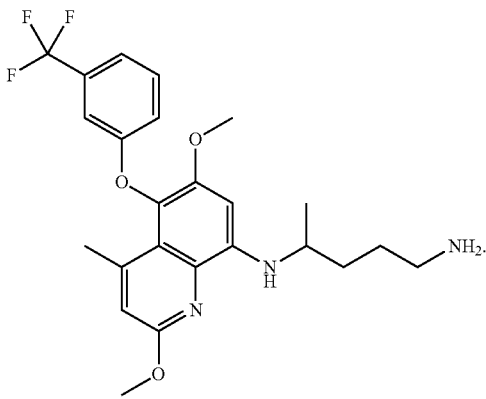

In one aspect, the method of prevention of malaria in a human subject comprises administering to the human subject one or more initial dose(s) (e.g., at least once per day for three days, once per week for one to three weeks, three times, or at least three times) prior to potential exposure of at least one species of *Plasmodium*, wherein each said initial dose is about 40 to about 399 mg; followed by administration of one or more exposure dose(s) of a compound or Formula (I), a pharmaceutically acceptable salt thereof, or a pharmaceutical composition comprising a compound of Formula (I), from about once per day to about once per week during potential exposure of at least one species of *Plasmodium*, wherein the total administered amount of the exposure dose is about 75 to about 399 mg per week, followed by administration of one or more post-exposure dose(s) of a compound of Formula (I), a pharmaceutically acceptable salt thereof, or a pharmaceutical composition comprising a compound of Formula (I), (e.g., one or more times, at least once per day for three days, once per week for three weeks, three times, or at least three times) after potential exposure of at least one species of *Plasmodium*; wherein each said post-exposure dose is about 40 to about 399 mg, and wherein the human subject is malaria-naïve and G6PD normal. In certain embodiments, the initial dose(s) is administered to achieve prior to potential exposure, the exposure doses are administered to maintain during potential exposure, and the post-exposure dose(s) is administered to maintain for at least three weeks after potential exposure, a serum or plasma concentration of a compound of Formula (I) or tafenoquine of between about 50 ng/mL and about 400 ng/mL in the subject. In other embodiments, the serum or plasma concentration achieved in the subject is at least about 50 ng/mL, 80 ng/mL, 100 ng/mL, 125 ng/mL, 150 ng/mL, or 175 ng/mL of tafenoquine or a compound of Formula (I). In certain aspects, the serum or plasma concentration is measured as the median C min of a population of subjects administered the given dose of a compound of Formula (I). In other aspects, the serum or plasma concentration is measured as the $5^{th}$ percentile C min of a population of subjects administered the given dose of a compound of Formula (I). In further aspects, the serum or plasma concentration of a compound of Formula (I), or tafenoquine is measured in the individual subject.

In another aspect of the invention, the method of prevention of malaria in a human subject is a method of prevention of post-exposure malaria and comprises administering to the human subject one or more primary dose(s) of a compound of Formula (I), a pharmaceutically acceptable salt thereof, or a pharmaceutical composition comprising a compound of Formula (I), one or more times, for example at least once per day for three days, once per week for one to three weeks, or three times, wherein each said primary dose is about 40 to about 399 mg; followed by administering to the human subject a post-exposure dose of a compound of Formula (I), a pharmaceutically acceptable salt thereof, or a pharmaceutical composition comprising a compound of Formula (I), one or more times after potential exposure; wherein each said post-exposure dose is about 40 to about 399 mg, and wherein the human subject is malaria-naïve and G6PD normal. In certain embodiments, the primary dose(s) is administered to achieve, and the post-exposure dose(s) is administered to maintain for at least three weeks after potential exposure, a serum or plasma concentration of a compound of Formula (I) or tafenoquine of between about 50 ng/mL and about 400 ng/mL in the subject. In other embodiments, the serum or plasma concentration achieved in the subject is at least about 50 ng/mL, 80 ng/mL, 100 ng/mL, 125 ng/mL, 150 ng/mL, or 175 ng/mL of tafenoquine or a compound of Formula (I). In certain aspects, the serum or plasma concentration is measured as the median C min of a population of subjects administered the given dose of a compound of Formula (I). In other aspects, the serum or plasma concentration is measured as the $5^{th}$ percentile C min of a population of subjects administered the given dose of a compound of Formula (I). In further aspects, the serum or plasma concentration of a compound of Formula (I), or tafenoquine is measure in the individual subject.

In one embodiment, the initial doses are administered at intervals of about once per day. In further embodiments, the initial doses are administered at intervals of about once every two to six days. In yet other embodiments, the initial doses are administered at intervals of about every two days. In another embodiment, the initial doses are administered at intervals of about every three days. In yet other embodiments, the initial doses are administered at intervals of about every four days. In further embodiments, the initial doses are administered at intervals of about every five days. In still another embodiment, the initial doses are administered at intervals of about every six day. In other embodiments, the initial doses are administered at intervals of about once per week. In further embodiments, the initial doses are administered at least three times. In other embodiments, the initial doses are administered for about one week, about two weeks, or about three weeks. In yet other embodiments, the initial doses are divided doses that are administered about two to about four times per day. In other embodiments, the initial doses are divided doses that are administered about two, three, or four times per day.

In certain embodiments, the initial doses are administered for about 1-21 days. In other embodiments, the initial doses are administered for about 1-14 days, 1-10 days, 1-7 days, 1-5 days, or 1-3 days. In yet other embodiments, the initial doses are administered for about 1, 2, 3, 4, 5, 6, 7, 8, 9, 10, 11, 12, 13, 14, 15, 16, 17, 18, 19, 20, or 21 days.

In one embodiment, the exposure doses are administered at intervals of about once per day. In further embodiments, the exposure doses are administered at intervals of about once every two to six days. In further embodiments, the exposure doses are administered at intervals of about every two days. In another embodiment, the exposure doses are administered at intervals of about every three days. In yet other embodiments, the exposure doses are administered at intervals of about every four days. In further embodiments, the exposure doses are administered at intervals of about every five days. In another embodiment, the exposure doses are administered about every six days. In other embodiments, the exposure doses are administered at intervals of about once per week. In further embodiments, the exposure doses are divided doses that are administered about two to about four times per day. In yet other embodiments, the exposure doses are divided doses that are administered about 2, 3, or 4 times per day.

In certain embodiments of the invention, the initial dose, the exposure dose, the primary dose, and/or the post-exposure dose is about 10 to about 399 mg and is administered at various frequencies per week from once every day up to once every seven days, wherein the total amount of exposure dose administered in a week is about 75 to about 399 mg. In further embodiments, the initial dose, the exposure dose, the primary dose, and/or the post-exposure dose is about 10 to about 57 mg and is administered about once per day. In some embodiments, the initial dose, the exposure dose, the primary dose, and/or the post-exposure dose is about 15, about 20, about 25, about 30, about 35, about 40, about 45, about 50, or about 55 mg and is administered once per day. In still other embodiments, the initial dose, the primary dose, and/or the post-exposure dose is about 57 to about 399 mg and is administered about once per day. In further embodiments, the initial dose, the primary dose, and/or the post-exposure dose is about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 200, about 205, about 210, about 215, about 220, about 225, about 230, about 235, about 240, about 245, about 250, about 255, about 260, about 265, about 270, about 275, about 280, about 285, about 290, about 295, about 300, about 305, about 310, about 315, about 320, about 325, about 330, about 335, about 340, about 345, about 350, about 355, about 360, about 365, about 370, about 375, about 380, about 385, about 390, or about 395 mg and is administered once per day. In yet other embodiments, the initial dose, the exposure dose, the primary dose, and/or the post-exposure dose is about 21 to about 114 mg and is administered about once every two days. In some embodiments, the initial dose, the exposure dose, the primary dose, and/or the post-exposure dose is about 25, about 30, about 35, about 40, about 45, about 50, about 55, about 60, about 65, about 70, about 75, about 80, about 85, about 90, about 95, about 100, about 105, or about 110 mg and is administered about once every two days. In still other embodiments, the initial dose, the primary dose, and/or the post-exposure dose is about 114 to about 399 mg and is administered about once every two days. In still other embodiments, the initial dose, the primary dose, and/or the post-exposure dose is about 115, about 120, about 125, about 130, about 135, about 140, about 145, about 150, about 155, about 160, about 165, about 170, about 175, about 180, about 185, about 190, about 200, about 205, about 210, about 215, about 220, about 225, about 230, about 235, about 240, about 245, about 250, about 255, about 260, about 265, about 270, about 275, about 280, about 285, about 290, about 295, about 300, about 305, about 310, about 315, about 320, about 325, about 330, about 335, about 340, about 345, about 350, about 355, about 360, about 365, about 370, about 375, about 380, about 385, about 390, or about 395 mg and is administered every two days. In further embodiments, the initial dose, the exposure dose, the primary dose, and/or the post-exposure dose is about 32 to about 171 mg and is administered about once every three days. In some embodiments, the initial dose, the exposure dose, the primary dose, and/or the post-exposure dose is about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, or about 170 mg and is administered about once every three days. In still other embodiments, the initial dose, the primary dose, and/or the post-exposure dose is about 171 to about 399 mg and is administered about once every three days. In further embodiments, the initial dose, the primary dose, and/or the post-exposure dose is about 175, about 180, about 185, about 190, about 200, about 205, about 210, about 215, about 220, about 225, about 230, about 235, about 240, about 245, about 250, about 255, about 260, about 265, about 270, about 275, about 280, about 285, about 290, about 295, about 300, about 305, about 310, about 315, about 320, about 325, about 330, about 335, about 340, about 345, about 350, about 355, about 360, about 365, about 370, about 375, about 380, about 385, about 390, or about 395 mg and is administered once every three days. In yet other embodiments, the initial dose, the exposure dose, the primary dose, and/or the post-exposure dose is about 42 to about 230 mg and is administered about once every four days. In some embodiments, the initial dose, the exposure dose, the primary dose, and/or the post-exposure dose is about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 200, about 205, about 210, about 215, about 220, or about 225 mg and is administered about once every four days. In still other embodiments, the initial dose, the primary dose, and/or the post-exposure dose is about 230 to about 399 mg and is administered about once every four days. In further embodiments, the initial dose, the primary dose, and/or the post-exposure dose is about 230, about 235, about 240, about 245, about 250, about 255, about 260, about 265, about 270, about 275, about 280, about 285, about 290, about 295, about 300, about 305, about 310, about 315, about 320, about 325, about 330, about 335, about 340, about 345, about 350, about 355, about 360, about 365, about 370, about 375, about 380, about 385, about 390, or about 395 mg and is administered once every four days. In other embodiments, the initial dose, the exposure dose, the primary dose, and/or the post-exposure dose is about 53 to about 285 mg and is administered about once every five days. In some embodiments, the initial dose, the exposure dose, the primary dose, and/or the post-exposure dose is about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 200, about 205, about 210, about 215, about 220, about 225, about 230, about 235, about 240, about 245, about 250, about 255, about 260, about 265, about 270, about 275, or about 280 mg and is administered about once every five days. In still other embodiments the initial dose, the primary dose, and/or the post-exposure dose is about 285 to about 399 mg and is administered once every five days. In other embodiments, the initial dose, the primary dose, and/or the post-exposure dose is about 285, about 290, about 295, about 300, about 305, about 310, about 315, about 320, about 325, about 330, about 335, about 340, about 345, about 350, about 355, about 360, about 365, about 370, about 375, about 380, about 385, about 390, or about 395 mg and is administered once every five days. In further embodiments, the initial dose, the exposure dose, the primary dose, and/or the post-exposure dose is about 64 to about 342 mg and is administered about once every six days. In some embodiments, the initial dose, the exposure dose, the primary dose, and/or the post-exposure dose is about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 200, about 205, about 210, about 215, about 220, about 225, about 230, about 235, about 240, about 245, about 250, about 255, about 260, about 265, about 270, about 275, about 280, about 285, about 290, about 295, about 300, about 305, about 310, about 315, about 320, about 325, about 330, about 335, or about 340 mg and is administered about once every six days. In still other embodiments, the initial doses, the primary dose, and/or the post-exposure dose is about 342 to about 399 mg and is administered about once every six days. In other embodiments, the initial dose, the primary dose, and/or the post-exposure dose is about 345, about 350, about 355, about 360, about 365, about 370, about 375, about 380, about 385, about 390, or about 395 mg and is administered once every six days. In yet other embodiments, the initial dose, the exposure dose, the primary dose, and/or the post-exposure dose is about 75 to about 399 mg and is administered about once every week. In some embodiments, the initial dose, the exposure dose, the primary dose, and/or the post-exposure dose is about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 200, about 205, about 210, about 215, about 220, about 225, about 230, about 235, about 240, about 245, about 250, about 255, about 260, about 265, about 270, about 275, about 280, about 285, about 290, about 295, about 300, about 305, about 310, about 315, about 320, about 325, about 330, about 335, about 340, about 345, about 350, about 355, about 360, about 365, about 370, about 375, about 380, about 385, about 390, or about 395 mg and is administered about once every week.

In one embodiment, the post-exposure doses are administered at intervals of about once per day for one to three days. In other embodiments, the post-exposure doses are administered at intervals of about once per day for one to three weeks. In further embodiments, the post-exposure doses are administered at intervals of about once every two to six days. In other embodiments, the post-exposure doses are administered at intervals of about every two days. In another embodiment, the post-exposure doses are administered at intervals of about every three days. In yet other embodiments, the post-exposure doses are administered at intervals of about every four days. In further embodiments, the post-exposure doses are administered at intervals of about every five days. In still other embodiments, the post-exposure doses are administered at intervals of about every six days. In other embodiments, the post-exposure doses are administered at intervals of about once a week. In further embodiments of the invention, the post-exposure doses are administered one, two, or three times. In other embodiments, the post-exposure doses are administered for about one week, about two weeks, or about three weeks. In another embodiment, the post-exposure doses are administered for about one to three weeks. In yet other embodiments, the post-exposure doses are administered for at least three weeks after exposure to at least one species of *Plasmodium*. In further embodiments, the post-exposure doses are divided doses that are administered about two to about four times per day. In yet other embodiments, the post-exposure doses are divided doses that are administered about 2, 3, or 4 times per day.

In certain embodiments, the post-exposure doses are administered for about 1-21 days. In other embodiments, the post-exposure doses are administered for about 1-14 days, 1-10 days, 1-7 days, 1-5 days, or 1-3 days. In yet other embodiments, the post-exposure doses are administered for about 1, 2, 3, 4, 5, 6, 7, 8, 9, 10, 11, 12, or 13 days.

In one embodiment, the primary doses are administered at intervals of about once per day. In further embodiments, the primary doses are administered at intervals of about once every two to six days. In other embodiments, the primary doses are administered at intervals of about every two days. In some embodiments, the primary doses are administered at intervals of about every three days. In yet other embodiments, the primary doses are administered at intervals of about every four days. In another embodiment, the primary doses are administered at intervals of about every five days. In still another embodiment, the primary doses are administered at intervals of about every six days. In other embodiments, the primary doses are administered at intervals of about once a week. In other embodiments, the primary doses are administered for about one week, about two weeks, or about three weeks. In another embodiment, the primary doses are administered for about one to three weeks. In yet other embodiments, the primary doses are administered for at least three weeks. In further embodiments, the primary doses are administered at least three times. In yet other embodiments, the primary doses are divided doses that are administered about two to about four times per day. In yet other embodiments, the primary doses are divided doses that are administered about 2, 3, or 4 times per day.

In certain embodiments, the primary doses are administered for about 1-21 days. In other embodiments, the primary doses are administered for about 1-14 days, 1-10 days, 1-7 days, 1-5 days, or 1-3 days. In yet other embodiments, the primary doses are administered for about 1, 2, 3, 4, 5, 6, 7, 8, 9, 10, 11, 12, 13, 14, 15, 16, 17, 18, 19, 20, or 21 days.

In certain embodiments, the total amount of the initial dose administered does not exceed about 900, 600, 500, or 400 mg prior to potential exposure of at least one species of Plasmodium. In other embodiments, the total average weekly exposure dose does not exceed about 200 mg. In further embodiments, the total average weekly exposure dose does not exceed 299 mg.

In certain embodiments, the initial dose is about 40-100 mg administered once per day for six days, followed by the exposure dose of about 12 mg, about 15 mg, about 20 mg, about 25 mg, about 30 mg, or about 35 mg, about 40 mg, or about 42 mg administered once per day during potential exposure to at least one species of Plasmodium. In other embodiments, the initial dose is between about 34 and 85 mg administered once per day for seven days, followed by the exposure dose of about 12 mg, about 15 mg, about 20 mg, about 25 mg, about 30 mg, about 35 mg, about 40 mg, or about 42 mg administered once per day during potential exposure to at least one species of Plasmodium. In other embodiments, the initial dose is between about 48 and 120 mg administered once per day for five days, followed by the exposure dose of about 12 mg, about 15 mg, about 20 mg, about 25 mg, about 30 mg, about 35 mg, about 40 mg, or about 42 mg administered once per day during potential exposure to at least one species of Plasmodium. In other embodiments, the initial dose is between about 60 and 150 mg administered once per day for four days, followed by the exposure dose of about 12 mg, about 15 mg, about 20 mg, about 25 mg, about 30 mg, about 35 mg, about 40 mg, or about 42 mg administered once per day during potential exposure to at least one species of Plasmodium. In other embodiments, the initial dose is between about 80 and 200 mg administered once per day for three days, followed by the exposure dose of about 12 mg, about 15 mg, about 20 mg, about 25 mg, about 30 mg, about 35 mg, about 40 mg, or about 42 mg administered once per day during potential exposure to at least one species of Plasmodium. In other embodiments, the initial dose is between about 30-35 mg administered once per day for seven days, followed by the exposure dose of about 30-35 mg administered once per day during potential exposure to at least one species of Plasmodium.

In other embodiments, the initial dose of about 100 mg is administered once per day for six days, followed by the exposure dose of about 100 mg administered once every four days during potential exposure to at least one species of Plasmodium.

In various embodiments, the post-exposure dose is administered. In further embodiments, the post-exposure dose is administered one or more times, e.g., one, two, or at least three times. In further embodiments, the total weekly amount of administered exposure dose is between about 75 and about 175 mg and the post-exposure dose is administered. In yet other embodiments, the total weekly amount of administered exposure dose is between about 175 mg and 195 mg and the post-exposure dose is not administered.

In the various embodiments, the human subject can be a malaria-naïve and G6PD-normal adult or a child.

In certain embodiments, the administration of the initial dose, exposure dose, post-exposure dose, and/or primary dose is in a suitable formulation based upon the human subject's body weight and/or age. In further embodiments, the human subject has a low body weight. In still other embodiments, the initial dose, the exposure dose, the post-exposure dose, and/or the primary dose are administered in concentration amounts of mg/kg based upon the individual subject's weight, for example about 1-5 mg/kg.

The compound of Formula (I) is represented by the following structure:

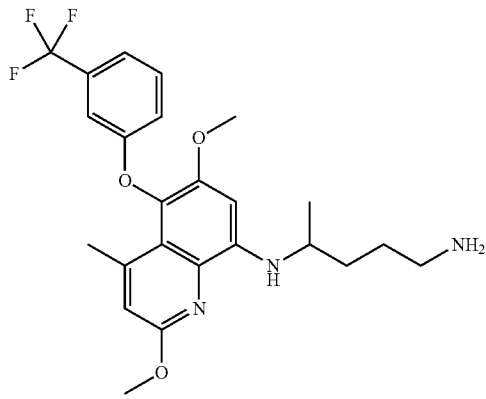 [SMILES: COc1cc(C)c2c(Oc3cccc(C(F)(F)F)c3)c(OC)cc(NC(C)CCCN)c2n1]

or a pharmaceutically acceptable salt thereof.

In preferred embodiments, the compound of Formula (I) is Tafenoquine (TQ), a pharmaceutically acceptable salt of Tafenoquine, or is represented by the following structure:

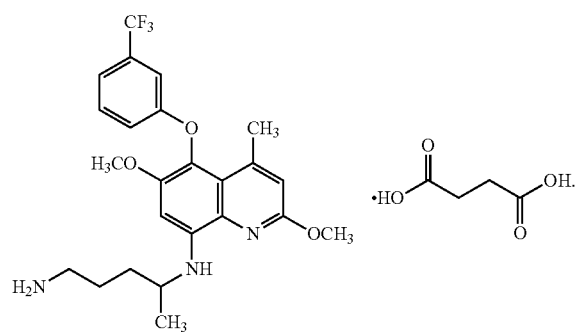

In certain embodiments, the initial doses are the same as either the exposure doses or the post-exposure doses, while in other embodiments the initial doses differ from either the exposure doses or the post-exposure doses. In further embodiments, the exposure doses are the same as the post-exposure doses, while in other embodiments the exposure doses differ from the post-exposure doses. In yet other embodiments, the primary doses are the same as the post-exposure doses, while in other embodiment the primary doses differ from the post-exposure doses.

In certain embodiments, for a malaria-naïve and G6PD-normal human subject, the initial doses of a compound of Formula (I), a pharmaceutically acceptable salt of Formula (I), or a pharmaceutical composition comprising a compound of Formula (I) can be between about 75 to about 399 mg. In other embodiments, the initial doses can be about 100-399 mg, about 150-399 mg, about 200-399 mg, or about 250-399 mg. In further embodiments, the initial doses can be about 75 mg, about 100 mg, about 125 mg, about 150 mg, about 175 mg, about 190 mg, about 200 mg, about 210, about 225 mg, about 250 mg, about 275 mg, about 300 mg, about 325 mg, about 350 mg, about 375 mg, or about 399 mg. In a further embodiment, the initial doses in a human subject are between about 350 and about 399 mg. In another embodiment, the initial doses in a human subject are between about 300 and about 350 mg. In yet another embodiment, the initial doses in a human subject are between about 250 and about 300 mg. In further embodiment, the initial doses in a human subject are between about 200 and about 250 mg. In yet another embodiment, the initial doses in a human subject are between about 210 and about 250 mg. In another embodiment, the initial doses of a compound of Formula (I) in a human subject are between about 150 and about 200 mg. In yet other embodiments, the initial doses of a compound of Formula (I) in a human subject are between about 175 and about 195. In further embodiments of the invention, the initial doses in a human subject are between about 190 and about 150 mg. In further embodiment, the initial doses in a human subject are between about 100 and about 150 mg. In another embodiment, the initial doses in a human subject are between about 75 and about 125 mg.

The exposure doses of a compound of Formula (I), a pharmaceutically acceptable salt of Formula (I), or a pharmaceutical composition comprising a compound of Formula (I) is administered to a malaria-naïve and G6PD-normal human subject can total between about 75 and about 399 mg in a week. In further embodiments, a total of about 75 mg, about 100 mg, about 125 mg, about 150 mg, about 175 mg, about 190 mg, about 200 mg, about 210 mg, about 225 mg, about 250 mg, about 275 mg, about 300 mg, about 325 mg, about 350 mg, about 375 mg, or about 399 mg of the exposure dose is administered to the human subject in a week. In one embodiment, a total of about 350 to about 399 mg of the exposure dose is administered to a human subject in a week. In another embodiment, a total of about 300 to about 350 mg of the exposure dose is administered to a human subject in a week. In further embodiment, a total of about 250 to about 300 mg of the exposure dose is administered to a human subject in a week. In another embodiment, a total of about 200 to about 250 mg of the exposure dose is administered to a human subject in a week. In further embodiment, a total of about 210 to about 250 mg of the exposure dose is administered to a human subject in a week. In yet another embodiment, a total of about 150 to about 200 mg of the exposure dose is administered to a human subject in a week. In another embodiment, a total of about 150 to about 190 mg of the exposure dose is administered to a human subject in a week. In further embodiment, a total of about 100 to about 150 mg of the exposure dose of a compound is administered to a human subject in a week. In an additional embodiment, a total of about 125 to about 175 mg of the exposure dose is administered to a human subject in a week. In another embodiment, a total of about 175 to about 195 mg of the exposure dose is administered to a human subject in a week. In other embodiments, a total of about 75 to about 125 mg of the exposure dose is administered to a human subject in a week. In yet another embodiment, a total of about 150 mg of the exposure dose is administered to a human subject in a week.

The post-exposure doses of a compound of Formula (I), a pharmaceutically acceptable salt of Formula (I), or a pharmaceutical composition comprising a compound of Formula (I) in a malaria-naïve and G6PD-normal human subject can be between about 75 and about 399 mg. In other embodiments, the post-exposure doses can be about 75-299 mg, about 100-299 mg, about 150-299 mg, about 200-299 mg, about 100-399 mg, about 150-399 mg, about 200-399 mg, or about 250-399 mg. In further embodiments, the post-exposure doses can be about 75 mg, about 100 mg, about 125 mg, about 150 mg, about 175 mg, about 190 mg, about 200 mg, about 210 mg, about 225 mg, about 250 mg, about 275 mg, about 300 mg, about 325 mg, about 350 mg, about 375 mg, or about 399 mg. In a further embodiment, the post-exposure doses in a human subject are between about 350 to about 399 mg. In another embodiment, the post-exposure doses in a human subject are between about 300 and about 350 mg. In yet another embodiment, the post-exposure doses in a human subject are between about 250 and about 300 mg. In further embodiment, the post-exposure doses in a human subject are between about 200 and about 250 mg. In yet another embodiment, the post-exposure doses in a human subject are between about 210 and about 250 mg. In another embodiment, the post-exposure doses in a human subject are between about 150 and about 200 mg. In further embodiments of the invention, the post-exposure doses in a human subject are between about 150 and about 190 mg. In yet other embodiments, the post-exposure doses in a human subject are between about 175 and about 195 mg. In another embodiment, the post-exposure doses in a human subject are between about 75 and about 125. In further embodiment, the post-exposure doses in a human subject are between about 100 and about 150 mg.

In certain embodiments, for a malaria-naïve and G6PD-normal human subject, the primary doses of a compound of Formula (I), a pharmaceutically acceptable salt of Formula (I), or a pharmaceutical composition comprising a compound of Formula (I) can be between about 75 to about 399 mg. In other embodiments, the primary doses can be about 75-299 mg, about 100-299 mg, about 150-299 mg, about 200-299 mg, about 100-399 mg, about 150-399 mg, about 200-399 mg, or about 250-399 mg. In further embodiments, the primary doses can be about 75 mg, about 100 mg, about 125 mg, about 150 mg, about 175 mg, about 190 mg, about 200 mg, about 210 mg, about 225 mg, about 250 mg, about 275 mg, about 300 mg, about 325 mg, about 350 mg, about 375 mg, or about 399 mg. In a further embodiment, the primary doses in a human subject are between about 350 and about 399 mg. In another embodiment, the primary doses in a human subject are between about 300 and about 350 mg. In yet another embodiment, the primary doses in a human subject are between about 250 and about 300 mg. In further embodiment, the primary doses in a human subject are between about 200 and about 250 mg. In yet another embodiment, the primary doses in a human subject are between about 210 and about 250 mg. In other embodiments, the primary doses in a human subject are between about 175 and about 195 mg. In another embodiment, the primary doses in a human subject are between about 150 and about 200 mg. In further embodiments of the invention, the primary doses in a human subject are between about 150 and about 190 mg. In further embodiment, the primary doses in a human subject are between about 100 and about 150 mg. In still another embodiment, the primary doses in a human subject are between about 75 and about 125 mg.

In one embodiment, the initial doses are administered one to three weeks prior to potential exposure to at least one species of *Plasmodium*. In another embodiment, the initial doses are administered at least three days prior to potential exposure to at least one species of *Plasmodium*. In yet other embodiments, the initial doses are administered one, two, three, or at least three times prior to potential exposure to at least one species of *Plasmodium*.

In one embodiment, the post-exposure doses are administered one to three weeks after potential exposure to at least one species of *Plasmodium*. In another embodiment, the post-exposure doses are administered at least the three days after potential exposure to at least one species of *Plasmodium*. In yet other embodiments, the post-exposure doses are administered at least three times after potential exposure to at least one species of *Plasmodium*.

The compounds or pharmaceutical compositions of the present invention can be administered orally or sublingually. In one embodiment, the route of administration is oral. In yet another embodiment, the route of administration is sublingual.

The compounds or pharmaceutical compositions of the present invention can be administered as a single or as a divided dose. In some embodiments, the doses can be single, divided, or a combination thereof. For the initial doses, the exposure doses, the primary dose, and/or the post-exposure doses in one embodiment, the human subject is administered a divided dose of from about 12 to about 399 mg of a compound of Formula (I), or a pharmaceutical composition. In some embodiments of the invention, the human subject is administered a divided dose of the initial dose, the exposure dose, the primary dose, and/or the post-exposure dose about two to about four times a day.

The invention also relates to methods of preventing malaria by achieving and maintaining a steady state C min serum or plasma concentration of between about 50 ng/mL and about 800 ng/mL of Formula (I) or tafenoquine in approximately 90% of malaria-naïve, G6PD-normal adult or child subjects. In another aspect, methods of preventing malaria comprise achieving a steady state C min serum or plasma concentration of at least about 50 ng/mL to about 400 ng/mL prior to potential exposure of at least one species of *Plasmodium*. In certain embodiments, the steady state C min serum or plasma concentration is at least about 80 ng/mL to about 200 ng/mL prior to potential exposure of at least one species of *Plasmodium*. In other embodiments, the steady state C min serum or plasma concentration is at least about 100 ng/mL to about 175 ng/mL prior to potential exposure of at least one species of *Plasmodium*. In further embodiments, the steady state C min serum or plasma concentration of at least about 50 ng/mL to about 400 ng/mL is maintained throughout the period of potential exposure of at least one species of *Plasmodium*. In other embodiments, the steady state C min serum or plasma concentration of at least about 80 ng/mL to about 200 ng/mL is maintained throughout the period of potential exposure of at least one species of *Plasmodium*. In additional embodiments, the steady state C min serum or plasma concentration of at least about 100 ng/mL to about 175 ng/mL is maintained throughout the period of potential exposure of at least one species of *Plasmodium*. In yet another embodiment, the steady state C min serum or plasma concentration of at least about 50 ng/mL to about 400 ng/mL is maintained for at least three weeks after potential exposure of at least one species of *Plasmodium*. In other embodiments, the steady state C min serum or plasma concentration of at least about 80 ng/mL to about 200 ng/mL is maintained for at least three weeks after potential exposure of at least one species of *Plasmodium*. In further embodiments, the steady state C min serum or plasma concentration of at least about 100 ng/mL to about 175 ng/mL is maintained for at least three weeks after potential exposure of at least one species of *Plasmodium*. In further embodiment, prior to potential exposure, throughout the period of potential exposure, and/or for at least three weeks after potential exposure, the steady state C min serum or plasma concentration achieved and maintained in a malaria-naïve, G6PD-normal adult or child subject is between about 80 ng/mL to about 600 ng/mL of a compound of Formula (I) or tafenoquine. In another embodiment, a steady state C min serum or plasma concentration achieved and maintained for at least three weeks after potential exposure in a malaria-naïve, G6PD-normal adult or child subject is between about 80 ng/mL to about 400 ng/mL of a compound of Formula (I) or tafenoquine. In yet another embodiment, a steady state C min serum or plasma concentration achieved and maintained for at least three weeks after potential exposure in a malaria-naïve, G6PD-normal adult or child subject is between about 80 ng/mL to about 200 ng/mL of a compound of Formula (I) or tafenoquine. In another embodiment, a steady state C min serum or plasma concentration achieved and maintained for at least three weeks after potential exposure in a malaria-naïve, G6PD-normal adult or child subject is at least about 80 ng/mL of a compound of Formula (I) or tafenoquine. In other embodiments, a steady state C min serum or plasma concentration achieved and maintained for at least three weeks after potential exposure in a malaria-naïve, G6PD-normal adult or child subject is at least about 50 ng/mL, 80 ng/mL, 100 ng/mL, 125 ng/mL, 150 ng/mL, or 175 ng/mL of a compound of Formula (I) or tafenoquine. In certain embodiments, prior to exposure, throughout the period of exposure, and/or for at least three weeks after exposure, a steady state C min serum or plasma concentration achieved in a subject is at least about 50 ng/mL, 80 ng/mL, 100 ng/mL, 125 ng/mL, 150 ng/mL, or 175 ng/mL of a compound of Formula (I) or tafenoquine. In certain aspects, the C min is measured as the median C min of a population of subjects. In other aspects, the C min is measured as the $5^{th}$ percentile C min of a population of subjects. In still other aspects, the serum or plasma concentration of a compound of Formula (I) or tafenoquine is measured in the individual subject.

The invention is also directed to methods of preventing malaria comprising administering a pharmaceutical composition comprising a compound of Formula (I) or tafenoquine according to any one of the dosing regimens described herein. The disclosed compounds of Formula (I) or tafenoquine can be administered to the subject in conjunction with an acceptable pharmaceutical carrier or diluent as part of a pharmaceutical composition for prevention of malaria. The invention is further directed toward kits for administering the disclosed dosing regimens or for carrying the disclosed methods.

BRIEF DESCRIPTION OF THE DRAWINGS

The foregoing will be apparent from the following more particular description of example embodiments of the invention, as illustrated in the accompanying drawings.

FIG. 3 depicts the predicted $95^{th}$ percentile, median, and $5^{th}$ percentile plasma tafenoquine concentrations for a hypothetical oral intake of tafenquine for approximately six months of potential exposure to at least one species of *Plasmodium*, in which the regimen included an initial dose (200 mg once per day for three days), weekly exposure doses (200 mg), followed by three once weekly post-exposure doses (200 mg). This regimen maintains the 5th percentile tafenoquine concentrations at or above 80 ng/ml until approximately 3.5-4.5 weeks post-exposure. 80 ng/ml, depicted as a dotted horizontal line, is the threshold required for protection against development of symptomatic malaria in malaria-naïve, G6PD-normal individuals. Therefore, this dose is protective because median drug levels are higher than the 80 ng/ml threshold throughout deployment. The use of three once weekly post-exposure prophylaxis doses of 200 mg following potential exposure to at least one species of *Plasmodium* maintains drugs levels above 80 ng/ml at the $5^{th}$ percentile for several weeks post-deployment to prevent symptomatic malaria arising from a late deployment exposure to a species of *Plasmodium*.

Figure 3:
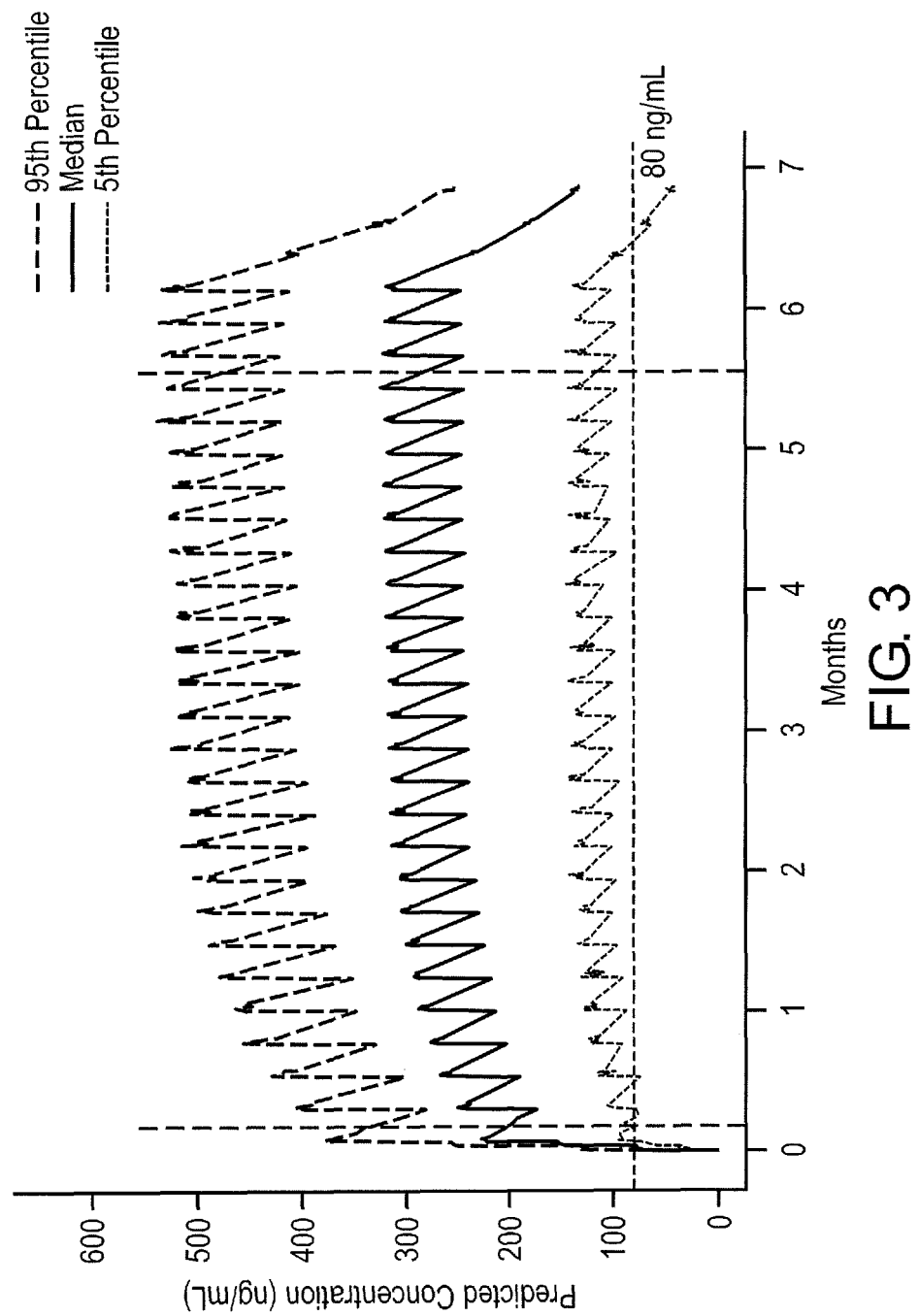
FIG. 3 Plasma concentration-time profile for tafenoquine following the Reference Regimen. The Reference Regimen consists of initial doses of 200 mg once daily for three days prior to exposure, followed by exposure doses of 200 mg once per week during exposure, and post-exposure doses of 200 mg once per week for three weeks post-exposure. The hashed horizontal line represents the 80 ng/mL concentration threshold. The left hashed vertical line represent when deployment and exposure doses begin. The period of time prior to the left hashed vertical line indicates the time during which initial doses are given. The right hashed vertical line represents when deployment ends and post-exposure dosing beings. Each peak represents the maximum concentration following administration of each new dose.
Figure 7:
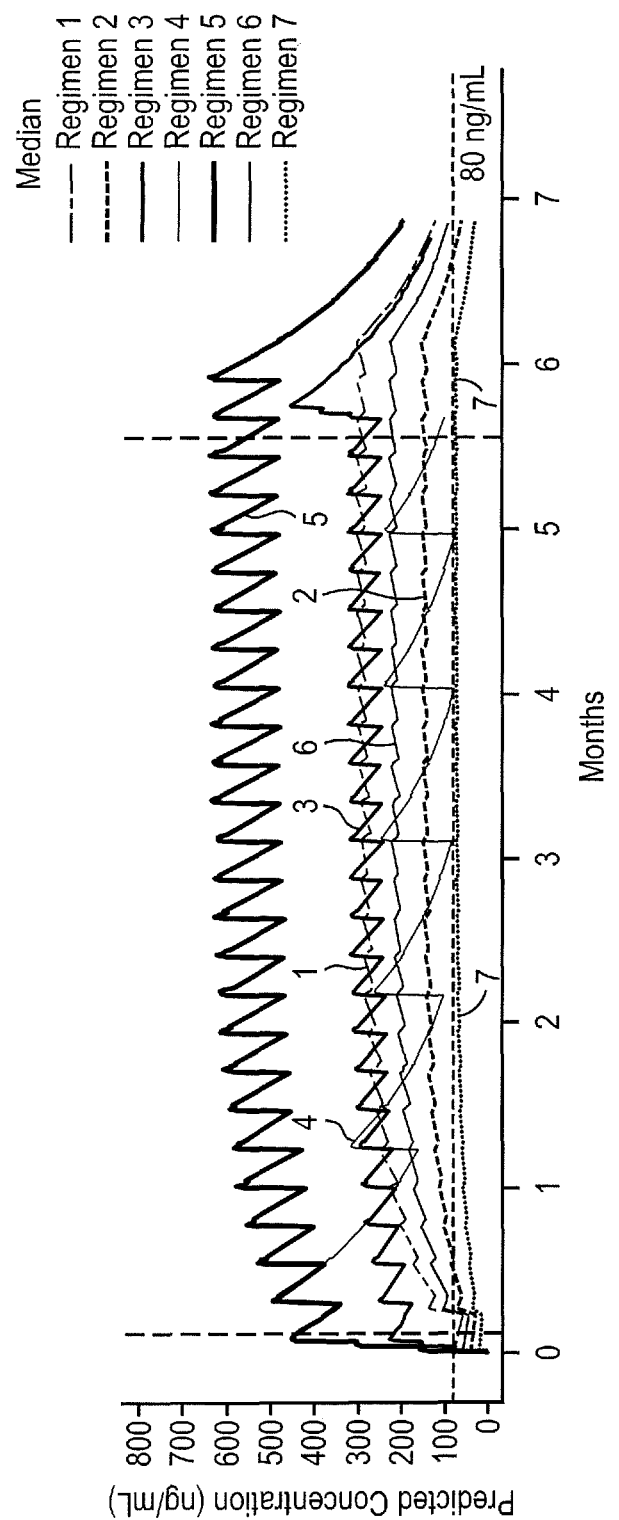
FIG. 7 Tafenoquine plasma concentration-time profiles (mean) following different regimens. Regimen 1 consists of 200 mg administered once weekly without an initial dose and Regimen 2 consists of 100 mg administered once weekly without an initial dose. Regimen 3 consists of an initial dose of 200 mg once daily for three days followed by a weekly dose of 200 mg for approximately five and a half months followed by three once-daily post-exposure doses. Regimen 4 consists of an initial dose administered once daily for three days followed by one weekly dose of 400 mg followed by a monthly exposure dose of 400 mg. Regimen 4 is similar to the dosing in the Walsh et. al. Thai marine study and was used for comparison purposes. Regimen 5 consists of a weekly dose of 400 mg following an initial dose of 400 mg once daily for three days. Regimen 6 consists of 150 mg administered once weekly without an initial dose and Regimen 7 consists of 50 mg administered once weekly without an initial dose. The hashed horizontal line represents the 80 ng/mL concentration threshold. The left hashed vertical line represents when deployment and exposure doses begin. The period of time prior to the left hashed vertical line indicates the time during which initial doses are given. The right hashed vertical line represents when deployment ends and post-exposure dosing beings. Each peak represents the maximum concentration following administration of each new dose.

Based on these profiles drawn in FIG. 7 and described on the prior page, the following conclusions can be drawn:

(i) Modification of the invention depicted in FIG. 3, by removing the initial dose (Regimen 1) maintains median minimum concentrations above the threshold provided that dosing is initiated at least three weeks prior to exposure. Modifying the Reference Regimen to allow administration of three doses of 200 mg not more than one week apart prior to potential exposure (rather than simply once per day) to at least one species of *Plasmodium*, will be better tolerated and reduce the risk of hemolytic anemia in G6PD, since the threshold dose considered safe in G6PD-deficient individuals is 300 mg. This general observation, that removing the initial dose maintains protection at the desired level is also true of other regimens, that are not 200 mg (see below), provided that dosing is initiated at an appropriate time prior to travel, deployment, or potential exposure to at least one species of *Plasmodium*.

(ii) Modification of the invention depicted in FIG. 3, by lowering the exposure dose to 100 or 150 mg (Regimens 2 or 6), does maintain median concentrations above the threshold for protection after two or three weekly doses. Simulation of the prophylactic monthly regimen of 400 mg (Regimen 4) predicted that median steady-state trough plasma tafenoquine concentrations above the threshold for protection did not persist for the entire simulated deployment and were lower than those of the reference regimen (FIG. 3). In the simulation in which 50 mg was given weekly with no initial dose (Regimen 7), median steady state trough concentrations never exceeded the intended threshold. Therefore the range of possible marketed doses is between 75-399 mg over the time period of a week (since Regimen 5, 400 mg, is poorly tolerated).

Figure 8:
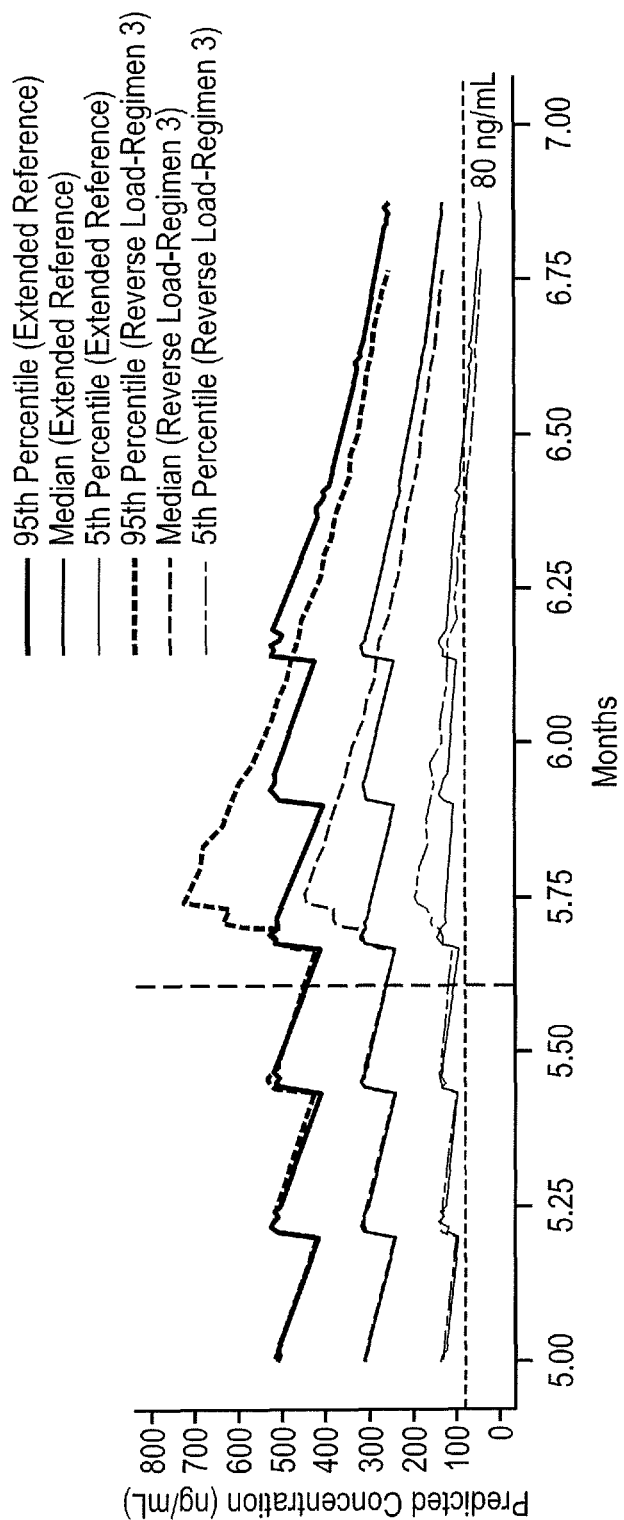

FIG. 8 Tafenoquine plasma concentration-time profiles ($95^{th}$, median, and $5^{th}$ percentiles) for additional time points. The extended Reference Regimen is the Reference Regimen viewed for an additional three weeks. The Reference Regimen consists of initial doses of 200 mg once daily for three days prior to exposure, followed by exposure doses of 200 mg once per week during exposure, and post-exposure doses 200 mg once per week for three weeks post-exposure (FIG. 3). Regimen 3, also referred to as reverse load, consists of 200 mg once-weekly doses followed by three once-daily doses. The hashed horizontal line represents the 80 ng/mL concentration threshold. The hashed vertical line represents when deployment ends. The area to the left of the hashed vertical line represents deployment and exposure doses. The area to the right of the hashed vertical line represents post-exposure dosing. Each peak represents the maximum concentration following administration of each new dose. This figure depicts the predicted $95^{th}$, median, and $5^{th}$ percentile tafenoquine plasma concentrations at the dose level depicted in FIG. 3 (solid lines) or a modified regimen (the 'reverse load' where the post-exposure dosing regimen is 200 mg once per day for three days, also Regimen 3 in FIG. 7). These regimens maintain plasma concentrations above the desired threshold for 2.5-3.5 weeks. The reverse load (Regimen 3) may be more convenient than post-exposure dosing once per week for three weeks. Since the peak observed after the reverse load is lower than that observed after dosing at 400 mg once per day for three days (see Regimen 5 in FIG. 7), it is expected to be better tolerated than the 400 mg regimen.

Figure 9:
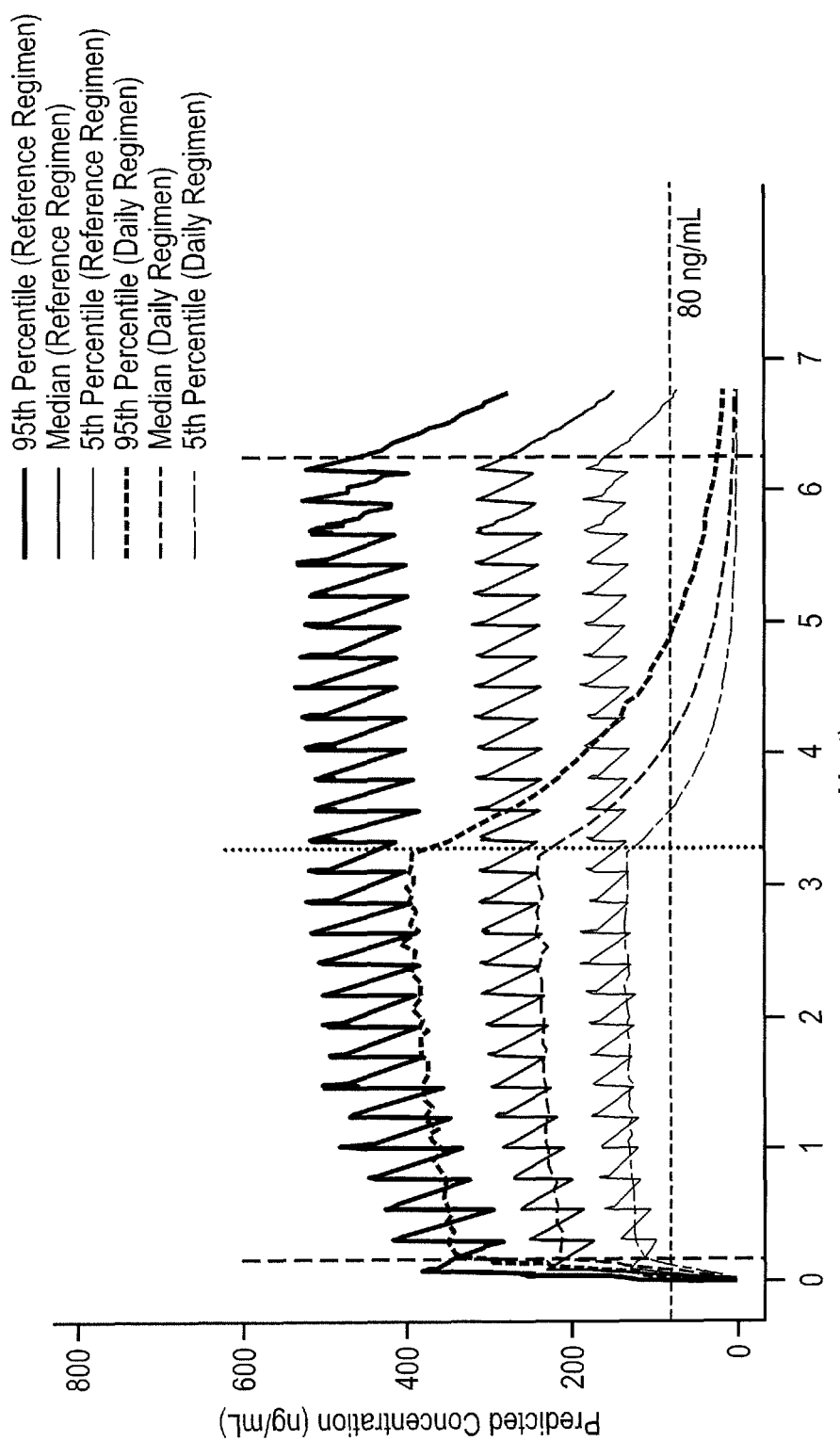

FIG. 9 Tafenoquine plasma concentration-time profiles. Profiles are depicted for a Daily Regimen (100 mg once per day for six days followed by 25 mg once per day for an approximately three month period during the period of exposure). For the purposes of comparison, profiles are depicted for the Reference Regimen (initial pre-exposure doses of 200 mg once per day for three days, followed by exposure doses of 200 mg per week during the period of exposure, and no post-exposure dose). The hashed horizontal line represents the 80 ng/mL concentration threshold. The hashed left vertical line represents when exposure dosing beings. The period of time prior to the left hashed vertical line indicates the initial doses. The right hashed vertical line represents when deployment ends for the Reference Regimen and the dotted vertical line represents when deployment ends for the Daily Regimen. Each peak indicates that a dose has been administered. The figure depicts an alternate way, via daily administration, of achieving steady state in a manner that is likely to improve gastrointestinal tolerability due to a reduction in the bolus dose of tafenoquine given at each dosing event (e.g., from 200 mg to 100 mg and 25 mg). Also it shows that with the Reference Regimen, and with this particular Daily Regimen, that post-exposure dosing is not required to maintain a median plasma concentration of at least 80 ng/mL for at least 3 weeks post-exposure.

DETAILED DESCRIPTION OF THE INVENTION

A description of example embodiments of the invention follows.

Definitions

All definitions of substituents set forth below are further applicable to the use of the term in conjunction with another substituent. Unless defined otherwise, all technical and scientific terms used herein have the same meaning as commonly understood by one of ordinary skill in the art to which this invention belongs.

As used herein, the singular forms "a," "and," and "the" include plural reference unless the context clearly dictates otherwise. Additionally, the term "comprises" is intended to include embodiments where the method, apparatus, composition, etc., consists essentially of and/or consists of the listed steps, components, etc. Similarly, the term "consists essentially of" is intended to include embodiments where the method, apparatus, composition, etc., consists of the listed steps, components, etc.

As used herein, the term "about" refers to a number that differs from the given number by less than 10%. In other embodiments, the term "about" indicates that the number differs from the given number by less than 9%, 8%, 7%, 6%, 5%, 4%, 3%, 2%, or 1%.

As used herein, "C min" refers to the minimum concentration that a drug achieves after the drug has been administered and prior to the administration of a second or additional dose. Further, "C max," as used herein, refers to the maximum concentration.

As used herein, "exposure dose" refers to the dose(s) which is administered during potential exposure to at least one species of *Plasmodium*. Further, "maintenance dose" and "exposure dose" have the same meaning and are used interchangeably herein.

As used herein, "G6PD-normal" refers to human subjects with normal levels of glucose-6-phosphate dehydrogenase. Normal levels of G6PD may be determined by approved laboratory tests using validated methodology known to those skilled in the art.

As used herein, "initial dose" refers to the dose(s) which is administered prior to potential exposure to at least one species of *Plasmodium*. Further, "loading dose," "initial dose," and "pre-exposure dose" have the same meaning and are used interchangeably herein.

As used herein, a "malaria-naïve" subject is defined operationally as referring to a human child or adult subject, for whom a physician, nurse, or other qualified medical or public health professional may reasonably assume has not previously experienced an episode of symptomatic malaria based on a review of travel and/or medical history.

As used herein, "non-immune" refers to individuals who have had insufficient prior exposure to malaria to render them immune to the signs and symptoms of malaria when malaria parasites are confirmed by microscopy to be present. A non-immune individual may also be malaria-naïve if they have never been exposed to malaria before.

"Pharmaceutically acceptable carrier" means non-therapeutic components that are of sufficient purity and quality for use in the formulation of a composition of the invention that, when appropriately administered, typically do not produce an adverse reaction, and that are used as a vehicle for a drug substance (e.g., a compound of Formula (I)).

As used herein, "post-exposure dose" refers to the dose(s) which is administered after potential exposure to at least one species of Plasmodium.

As used herein, "post-exposure malaria" refers to malaria which is caused from the latent stages of at least one species of Plasmodium and/or wherein the symptoms of malaria begin after potential exposure or travel.

As used herein, "potential exposure," "deployment," and "travel" refers to the period of time between entry and exit of a human subject into/from a geographical area where they may be exposed to Anopheles mosquitoes harboring human malaria parasites.

As used herein, "primary dose" refers to the dose(s) which is administered prior to the post-exposure dose and may be administered prior to or during potential exposure to at least one species of Plasmodium, or after potential exposure but prior to becoming symptomatic.

As used herein, "semi-immune" refers to a resident of a malaria-endemic country who, due to many prior exposures to symptomatic malaria, has developed a partial immunity that usually results in a lack of signs and symptoms of clinical malaria when the presence of malaria parasites in the blood is confirmed by microscopy.

As used herein, Formula (I) is "tafenoquine" and also includes the following references to tafenoquine: Tafenoquine, Tafenoquine [INN:BAN], Etaquine, UNII-262P8GS9L9, C24H28F3N303, CHEBI:172505, AIDS006901, 106635-81-8 (maleate), AIDS-006901, CID115358, SB-252263, WR 238605, WR-238605, WR238605, LS-172012, 1,4-Pentanediamine, N4-(2,6-dimethoxy-4-methyl-5-(3-(trifluromethyl)phenoxy)-8-quinolinyl-, 106635-80-7, N(4)-(2,6-Dimethoxy-4-methyl-5-((3-trifluromethyl)phenoxy)-8-quinolinyl)-1,4-pentanediamine, N-[2,6-dimethoxy-4-methyl-5-[3-(trifluoromethyl)phenoxy]quinolin-8-yl]diamine, (4-Amino-1-methylbutyl){2,6-dimethoxy-4-methyl-5-[3-(trifluoromethyl)phenoxy](8-quinolyl)}amine, (R)—N3-(2,6-Dimethoxy-4-methyl-5-(3-trifluoromethyl)phenoxy)quinolin-8-yl)pentane-1,4-diamine, (RS)—N(sup 3)-(2,6-Dimethoxy-4-methyl-5-(3-trifluoro-methylphenoxy)quinolin-8-yl)pentane-1,4-diamine.

Dosing Regimen

In certain embodiments, dosing is selected to provide a serum or plasma tafenoquine concentration of at least about 80 ng/mL. Doses above 400 mg are often not well tolerated (e.g., the dose may cause gastrointestinal issues or toxicity) by adult subjects regardless of the subjects' G6PD status. In G6PD normal adult subjects, doses of up to 400 mg may be well tolerated, while in G6PD deficient subjects, doses of 300 mg or more may not be well tolerated.

In one aspect, the method comprises administering to the human subject one or more initial dose(s) of a compound of Formula (I), a pharmaceutically acceptable salt thereof, or a pharmaceutical composition comprising a compound of Formula (I), for example, at least once per day for three days, once per week for one to three weeks, or at least three times, prior to potential exposure of at least one species of Plasmodium, wherein each said initial dose is about 75 to about 299 mg, followed by administering to the human subject an exposure dose of a compound of Formula (I), a pharmaceutically acceptable salt thereof, or a pharmaceutical composition comprising a compound of Formula (I), one or more times per week, for example once per day, once every two to six days, or once per week during potential exposure of at least one species of Plasmodium, wherein the total administered amount of the exposure dose is about 75 to about 299 mg per week, followed by administering to the human subject a post-exposure dose of a compound of Formula (I), a pharmaceutically acceptable salt thereof, or a pharmaceutical composition comprising a compound of Formula (I), for example, at least once per day for three days, once per week for three weeks, or at least three times, after potential exposure of at least one species of Plasmodium; wherein each said post-exposure dose is about 75 to about 299 mg, wherein the human subject is malaria-naïve and Glucose-6-phosphate dehydrogenase (G6PD) normal, and wherein Formula (I) has the following structure,

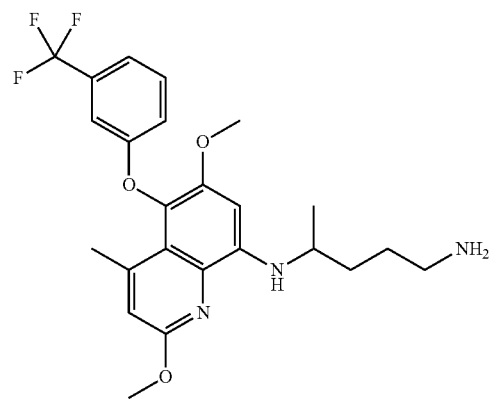 [SMILES: COc1cc(C)c2c(Oc3cccc(C(F)(F)F)c3)c(OC)cc(NC(C)CCCN)c2n1]

Alternative name: -[2,6-Dimethoxy-4-methyl-5-[3-(trifluoromethyl)phenoxy]quinolin-8-yl]pentane-1,4-diamine.

A pharmaceutically acceptable salt thereof, including,

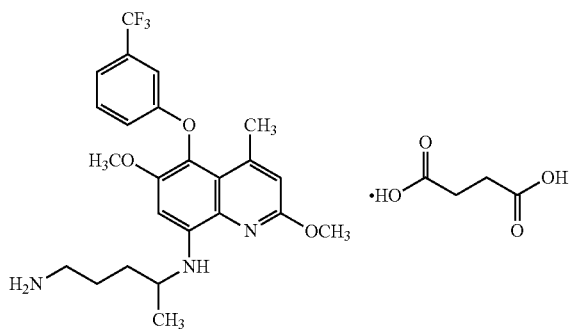

CAS number for above identified structure of succinate salt 106635-81-8.

The compounds of the invention useful for practicing the methods described herein may possess one or more chiral centers and so exist in a number of stereoisomeric forms. All stereoisomers and mixtures thereof are included in the scope of the present invention. Racemic compounds may either be separated using preparative HPLC and a column with a chiral stationary phase or resolved to yield individual enantiomers utilizing methods known to those skilled in the art. In addition, chiral intermediate compounds may be resolved and used to prepare chiral compounds of the invention.

The compounds described herein may exist in one or more tautomeric forms. All tautomers and mixtures thereof are included in the scope of the present invention.

The compounds of the present invention can be administered as the free base or as a pharmaceutically acceptable salt. For example, an acid salt of a compound of the present invention containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estotate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts. In one embodiment, the compound of Formula (I) is a hydrochloride salt.

The invention is also directed to methods of the invention using a pharmaceutical composition comprising a compound of Formula (I), or a pharmaceutically acceptable salt thereof. The disclosed compounds of Formula (I), or a pharmaceutically available salt thereof can be administered to the subject in conjunction with an acceptable pharmaceutical carrier or diluent as part of a pharmaceutical composition for prophylaxis of malaria, and according to any of the dosing regimens described herein. Formulation of the compound to be administered will vary according to the route of administration selected (e.g., solution, emulsion, capsule). Suitable pharmaceutical carriers may contain inert ingredients which do not interact with the compound. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986).

In one embodiment, the pharmaceutical composition comprises a pharmaceutically acceptable carrier or diluent and a compound of Formula (I), or a pharmaceutically acceptable salt thereof.

The methods of the invention prevent a human subject from having malaria. As used herein "preventing" or "prevention" refers to obtaining desired pharmacological and/or physiological effects. The effect can include achieving, partially or substantially, one or more of the following results: partially or totally avoiding the disease, disorder, or syndrome; or partially or totally avoiding clinical symptom or indicator associated with the disease, disorder, or syndrome.

The human subject may be an adult or a child. As used herein, a "child" refers to a human subject who is between the ages of 1 day to 17 years, 364 days of age inclusive. The term "adult" refers to a human subject who is 18 years of age or older.

Example embodiments of initial doses, exposure doses, and post-exposure doses in a human subject are shown in Table 1:

TABLE 1

Dosing Regimen for a Human Subject

| Embodiment | Initial dose (mg)[1] | Exposure dose (mg)[2] | Post-exposure dose (mg)[3] |
|---|---|---|---|
| 1 | 40 | 75, 100, 125, 150, 175, 190, 200, 210, 225, 250, 275, 300, 325, 350, 375, or 399 | 75, 100, 125, 150, 175, 190, 200, 210, 225, 250, 275, 300, 325, 350, 375, or 399 |
| 2 | 50 | 75, 100, 125, 150, 175, 190, 200, 210, 225, 250, 275, 300, 325, 350, 375, or 399 | 75, 100, 125, 150, 175, 190, 200, 210, 225, 250, 275, 300, 325, 350, 375, or 399 |
| 3 | 75 | 75, 100, 125, 150, 175, 190, 200, 210, 225, 250, 275, 300, 325, 350, 375, or 399 | 75, 100, 125, 150, 175, 190, 200, 210, 225, 250, 275, 300, 325, 350, 375, or 399 |
| 4 | 100 | 75, 100, 125, 150, 175, 190, 200, 210, 225, 250, 275, 300, 325, 350, 375, or 399 | 75, 100, 125, 150, 175, 190, 200, 210, 225, 250, 275, 300, 325, 350, 375, or 399 |
| 5 | 125 | 75, 100, 125, 150, 175, 190, 200, 210, 225, 250, 275, 300, 325, 350, 375, or 399 | 75, 100, 125, 150, 175, 190, 200, 210, 225, 250, 275, 300, 325, 350, 375, or 399 |
| 6 | 150 | 75, 100, 125, 150, 175, 190, 200, 210, 225, 250, 275, 300, 325, 350, 375, or 399 | 75, 100, 125, 150, 175, 190, 200, 210, 225, 250, 275, 300, 325, 350, 375, or 399 |
| 7 | 175 | 75, 100, 125, 150, 175, 190, 200, 210, 225, 250, 275, 300, 325, 350, 375, or 399 | 75, 100, 125, 150, 175, 190, 200, 210, 225, 250, 275, 300, 325, 350, 375, or 399 |
| 8 | 190 | 75, 100, 125, 150, 175, 190, 200, 210, 225, 250, 275, 300, 325, 350, 375, or 399 | 75, 100, 125, 150, 175, 190, 200, 210, 225, 250, 275, 300, 325, 350, 375, or 399 |
| 9 | 200 | 75, 100, 125, 150, 175, 190, 200, 210, 225, 250, 275, 300, 325, 350, 375, or 399 | 75, 100, 125, 150, 175, 190, 200, 210, 225, 250, 275, 300, 325, 350, 375, or 399 |
| 10 | 210 | 75, 100, 125, 150, 175, 190, 200, 210, 225, 250, 275, 300, 325, 350, 375, or 399 | 75, 100, 125, 150, 175, 190, 200, 210, 225, 250, 275, 300, 325, 350, 375, or 399 |

TABLE 1-continued

Dosing Regimen for a Human Subject

| Embodiment | Initial dose (mg)[1] | Exposure dose (mg)[2] | Post-exposure dose (mg)[3] |
|---|---|---|---|
| 11 | 225 | 75, 100, 125, 150, 175, 190, 200, 210, 225, 250, 275, 300, 325, 350, 375, or 399 | 75, 100, 125, 150, 175, 190, 200, 210, 225, 250, 275, 300, 325, 350, 375, or 399 |
| 12 | 250 | 75, 100, 125, 150, 175, 190, 200, 210, 225, 250, 275, 300, 325, 350, 375, or 399 | 75, 100, 125, 150, 175, 190, 200, 210, 225, 250, 275, 300, 325, 350, 375, or 399 |
| 13 | 275 | 75, 100, 125, 150, 175, 190, 200, 210, 225, 250, 275, 300, 325, 350, 375, or 399 | 75, 100, 125, 150, 175, 190, 200, 210, 225, 250, 275, 300, 325, 350, 375, or 399 |
| 14 | 300 | 75, 100, 125, 150, 175, 190, 200, 210, 225, 250, 275, 300, 325, 350, 375, or 399 | 75, 100, 125, 150, 175, 190, 200, 210, 225, 250, 275, 300, 325, 350, 375, or 399 |
| 15 | 325 | 75, 100, 125, 150, 175, 190, 200, 210, 225, 250, 275, 300, 325, 350, 375, or 399 | 75, 100, 125, 150, 175, 190, 200, 210, 225, 250, 275, 300, 325, 350, 375, or 399 |
| 16 | 350 | 75, 100, 125, 150, 175, 190, 200, 210, 225, 250, 275, 300, 325, 350, 375, or 399 | 75, 100, 125, 150, 175, 190, 200, 210, 225, 250, 275, 300, 325, 350, 375, or 399 |
| 17 | 375 | 75, 100, 125, 150, 175, 190, 200, 210, 225, 250, 275, 300, 325, 350, 375, or 399 | 75, 100, 125, 150, 175, 190, 200, 210, 225, 250, 275, 300, 325, 350, 375, or 399 |
| 18 | 399 | 75, 100, 125, 150, 175, 190, 200, 210, 225, 250, 275, 300, 325, 350, 375, or 399 | 75, 100, 125, 150, 175, 190, 200, 210, 225, 250, 275, 300, 325, 350, 375, or 399 |
| 19 | 75, 100, 125, 150, 175, 190, 200, 210, 225, 250, 275, 300, 325, 350, 375, or 399 | 75, 100, 125, or 150 | 75, 100, 125, 150, 175, 190, 200, 210, 225, 250, 275, 300, 325, 350, 375, or 399 |
| 20 | 75, 100, 125, 150, 175, 190, 200, 210, 225, 250, 275, 300, 325, 350, 375, or 399 | 175, 190, 200, 210, 225, 250, 275, 300, 325, 350, 375, or 399 | None |

[1]Initial dosing prior to potential exposure to at least one species of *Plasmodium* for a) once per day for up to ten days, b) once per week for three weeks, c) once per week for one week, d) at least three times, or e) divided doses thereof, including once every four days.
[2]Exposure dosing periodically during potential exposure to at least one species of *Plasmodium* for a) once per week during period of potential exposure, b) once per day during period of potential exposure, wherein the total administered amount over a week is listed above, c) once every two to six days doses thereof, wherein the total administered amount over a week is listed above, or d) divided doses thereof.
[3]Post-exposure dose administered after potential exposure to at least one species of *Plasmodium* for a) once per day for up to seven days, including once per day for three days b) once per week for three weeks, d) at least three times, or e) divided doses thereof, including once every four days.

In one embodiment of the invention, the compound of Formula (I) is tafenoquine or a pharmaceutically acceptable salt thereof.

In certain embodiments of the invention, the malaria-naïve, G6PD-normal human subject is an adult or a child.

In yet another embodiment, a steady state C min serum or plasma concentration of between about 50 ng/mL to about 800 ng/mL of tafenoquine in a malaria naïve, G6PD-normal human subject is attained. In further embodiment, a steady state C min serum or plasma concentration of between about 80 ng/mL to about 600 ng/mL of tafenoquine in a malaria naïve, G6PD-normal human subject is attained. In another embodiment, a steady state C min serum or plasma concentration of between about 80 ng/mL to about 400 ng/mL of tafenoquine in a malaria naïve, G6PD-normal human subject is attained. In yet another embodiment, a steady state C min serum or plasma concentration of between about 80 ng/mL to about 200 ng/mL of tafenoquine in a malaria naïve, G6PD-normal human subject is attained. In another embodiment, a steady state C min serum or plasma concentration of about greater than or equal to 80 ng/mL of tafenoquine in a malaria naïve, G6PD-normal human subject is attained. In certain embodiments the 80 ng/mL C min concentration will be that of the individual or of the median or $5^{th}$ percentile of a population administered the given dosing regimen.

In one embodiment of the invention, *Plasmodium* exposure comprises at least one *Plasmodium* species selected from *P. falciparum, P. vivax, P. ovale, P. malariae,* and *P. knowlesi*.

In yet another embodiment, administering the compound, or the pharmaceutical composition, achieves a steady state C min serum or plasma concentration of at least about 80 ng/mL of a compound of Formula (I) or tafenoquine. In other embodiments, administering the compound, or the pharmaceutical composition, achieves a steady state C min serum or plasma concentration of at least about 80 ng/mL of a compound of Formula (I) or tafenoquine which is maintained for at least three weeks after potential exposure of at least one species of *Plasmodium*. In further embodiment, administering the compound, or the pharmaceutical composition, achieves a steady state C min serum or plasma concentration of at least about 80 ng/mL of a compound of Formula (I) or tafenoquine in about greater than or equal to 50% of malaria naïve, G6PD-normal individuals.

The compounds of the present invention can be administered orally or sublingually. Oral and sublingual dosing can be in a single or divided dose.

The invention also relates to a method of preventing malaria by achieving a steady state C min serum or plasma concentration of at least about 80 ng/mL of tafenoquine in a malaria naïve, G6PD-normal human subject. As used herein, "C min" refers to the minimum concentration that a drug achieves after the drug has been administered and prior to the administration of a second or additional dose. Steady state C min is achieved when the overall intake of a drug C min concentration is fairly in dynamic equilibrium with its elimination. In some embodiments, C min concentration of a compound of Formula (I) or tafenoquine is determined at one or more points following treatment with techniques known in the art.

EXAMPLES

Example 1: Selection of Tafenoquine Doses for Malaria Prevention Utilizing a Pharmacokinetic-Pharmacodynamic Modeling Approach In a Phase III malaria prophylaxis study in non-immune (the vast majority of whom were also likely to have been malaria-naïve) Australian soldiers deployed on peacekeeping duties to Timor-Leste, a weekly regimen of 200 mg following administration of an initial dose of 200 mg daily for three days exhibited a protective efficacy of 100% (95% confidence interval [CI] of 93%-100%) (Nasveld P E et al., Randomized, double-blind study of the safety, tolerability, and efficacy of tafenoquine versus mefloquine for malaria prophylaxis in nonimmune subjects. *Antimicrob Agents Chemother.* 2010; 54:792-798; Dow G S, Mc Carthy W F, Reid M, Smith B, Tang D, Shanks D G. A retrospective analysis of the protective efficacy of tafenoquine and mefloquine as prophylactic anti-malarials in non-immune individuals during deployment to a malaria-endemic area. *Malaria Journal.* 2014, 13:49). The 200 mg dose selected for the Phase III study was the best tolerated of several effective regimens (50, 100, 200 and 400 mg) shown to provide statistically significant reductions in microscopically confirmed parasitemia in Phase II studies in a semi-immune African population (Shanks G D, Oloo A J, Aleman G M, et al. A new primaquine analogue, tafenoquine (WR 238605), for prophylaxis against *Plasmodium falciparum* malaria. *Clin Infect Dis.* 2001; 33:1968-1974; Hale B R, Owusu-Agyei S, Fryauff D J, et al. A randomized, double-blind, placebo-controlled, dose-ranging trial of tafenoquine for weekly prophylaxis against *Plasmodium falciparum*. *Clin Infect Dis.* 2003; 36:541-549). A dose of 400 mg tafenoquine is generally considered less well tolerated due to a higher frequency of gastrointestinal adverse events and methemoglobinemia.

Although the Phase III study in non-immune Australian soldiers demonstrated that a dose of 200 mg once per day for three days, followed by 200 mg once per week, prevented symptomatic malaria during potential exposure, the study did not address whether the treatment regimen would prevent the development of symptomatic malaria following travel due to exposure late in that period of travel and/or from a latent malarial infection. Thus, the present modeling study was undertaken to determine a dosing regimen that will provide adequate protection from post-exposure malarial infection and/or latent malarial infection throughout the three week period following exposure, when most post-exposure malarial infections or latent malarial infections arise.

Based on the observation in Phase II studies that symptomatic breakthroughs occurred when plasma tafenoquine concentrations were <40 ng/mL, the minimum protective threshold concentration of tafenoquine was set at 80 ng/mL in the present study (see, e.g., Shanks G D, Oloo A J, Aleman G M, et al. A new primaquine analogue, tafenoquine (WR 238605), for prophylaxis against *Plasmodium falciparum* malaria. *Clin Infect Dis.* 2001; 33:1968-1974; Hale B R, Owusu-Agyei S, Fryauff D J, et al. A randomized, double-blind, placebo-controlled, dose-ranging trial of tafenoquine for weekly prophylaxis against *Plasmodium falciparum*. *Clin Infect Dis.* 2003; 36:541-549; Llanos-Cuentas A, Lacerda M V, Rueangweerayut R, et al. Tafenoquine plus chloroquine for the treatment and relapse prevention of *Plasmodium vivax* malaria (DETECTIVE): a multicentre, double-blind, randomised, phase 2b dose-selection study. *Lancet.* 2014; 383:1049-1058).

Pharmacokinetic (PK) data from several studies (Phase I/II/III) was modeled to establish a consolidated model of tafenoquine and to determine relevant covariates. More specifically, analysis was performed using data obtained from ten Phase I/II/III clinical studies of tafenoquine (U.S. Army Study Numbers: 1, 2, 3, 4, 5, 14, 15, 33, 44 and 58). Table 2 summarizes the key features of each of the studies included in the pooled dataset such as the study type and design, dose and dosing regimen, population, and sample collection schemes. A total of 866 subjects were included in the population analysis. Ninety-three percent of the subjects were male. A demographic summary pooled across all of the available studies is presented in Table 3.

TABLE 2

Clinical Studies of Tafenoquine

| Study No. | N | Phase | Study Type | Study Design | Doses | Population | PK Collection |
|---|---|---|---|---|---|---|---|
| 1 | 45 | I | Single Dose Healthy Volunteer Study | Randomized, double-blind, placebo-controlled, single oral dose rising (fasted) | TQ 4 to 600 mg or placebo | 80 M healthy volunteers (18-35 y) | Before dosing and at 4, 8, 12, 24, 48, 72, 96 and 168 hr after dosing. For the six higher dose groups (250, 300-600 mg), additional samples were collected on Days 16, 23, 30 and 37. |

TABLE 2-continued

Clinical Studies of Tafenoquine

| Study No. | N | Phase | Study Type | Study Design | Doses | Population | PK Collection |
|---|---|---|---|---|---|---|---|
| 2 | 18 | I | Single Dose Healthy Volunteer Study | Randomized, parallel-group, single oral dose (fasted) | TQ 100, 200 or 400 mg | 18 M healthy volunteers (18-32 y) | N/A |
| 3 | 4 | I | Malaria Challenge Study in Healthy Volunteers | Randomized, double-blind, placebo-controlled, single dose, fasted, malaria challenge | TQ 600 mg (n = 4) or placebo (n = 2) 1 d before sporozoite inoculation | 4 M/2 F volunteers (19-30 y) | Before dosing and at 5, 7, 12, 28 and 42 d after dosing on Day 1 |
| 4 | 25 | I | Single and Repeat Dose Healthy Volunteer Study | Randomized, double-blind, placebo-controlled, multiple dose (fasted for ≥2 hr) | TQ 200, 400 or 600 mg or placebo weekly for 10 weeks | 30 M/6 F (23-46 y) | On Day 1 (Dose 1) and at Week 10 (Dose 10) before dosing and at 2, 4, 6, 8, 12, 16 and 24 hr after dosing. Additional trough blood samples were drawn pre-dose (weekly) prior to Doses 2 through 9 at Weeks 12, 14, 16, 18 and 20. |
| 5 | 10 | I | Malaria Challenge Study in Healthy Volunteers | Randomized, double-blind, placebo-controlled, multiple oral dose (fed) | TQ 600 mg or placebo on Days −3 and −2 before sporozoite inoculation (Day 0), then 300 mg on Days 3, 10, 17 and 24 | 12 M volunteers (19-36 y) | Before dosing on Day 17, before dosing on Day 24 and on Days 26, 31, 38, 45 and 59. |
| 14 | 58 | I | Relative Bioavailability in Healthy Volunteers | Randomized, relative bioavailability of 3 oral formulations | TQ 400 mg OD for 3 d (fed) | 43 M/15 F (21-60 y) | Relative to the first dose, blood samples were collected from each subject before dosing and up to 96 hr after dosing. Additional blood samples were collected on an ambulatory basis on Days 6, 7 and 8 and in Weeks 4, 6, 8, 10, 12, 14, 16 and 18. |
| 15 | 34 | I | Drug-Drug Interaction Studies in Healthy Volunteers | Single sequence, desipramine interaction | TQ 400 mg OD for 3 d (fed); desipramine 100 mg on morning of Day 1 and Day 11 (fasted) | 20 M/14 F (25-60 y) | Blood samples for determination of SB-252263 (TQ) plasma concentrations were collected up to 96 hr after the second dose of desipramine (Day 11) and thereafter at 2-week intervals until 9 weeks after the last (third) dose of SB-252263. |
| 33 | 491 | III | Malaria Prophylaxis Study | Double-blind, randomized, mefloquine positive control | TQ 200 mg for 3 d, then 200 mg weekly MQ 250 mg for 3 d, then 250 mg weekly | Non-immune Australian army troops 632 M/22 F (18-51 y) | During the prophylactic phase (Day 2 and Weeks 4, 8, 16 and 26) |
| 44 | 135 | II | Malaria Prophylaxis Study | Double-blind, randomized, placebo-controlled | TQ 400 mg for 3 d, then 400 mg monthly | Non-immune Royal Thai Army 104 M randomized to receive TQ and 101 M randomized to receive placebo | For the 104 soldiers on monthly TQ prophylaxis, blood samples were collected after commencing the loading dose at approximately 8, 24, 48 and 56 hr and then in intervals of 3 ± 4 d until the first monthly dose. After each monthly dose, samples were collected at approximately 8 hr after dosing, mid-month and at the end of the monthly dose (trough plasma drug concentration). Following the last monthly dose, samples were collected at approximately 4, 8, 12 and 24 hr and then in intervals of 3 ± 4 d for 2 months. At each blood collection, samples were obtained from 2 to 28 volunteers (mean ± SD, 12.6 ± 7.1 volunteers). For the 31 soldiers on weekly prophylaxis, blood samples were collected after 2 ± 22 weeks of medication (mean ± SD, 11.8 ± 6.8 weeks). Samples from this group were |

TABLE 2-continued

Clinical Studies of Tafenoquine

| Study No. | N | Phase | Study Type | Study Design | Doses | Population | PK Collection |
|---|---|---|---|---|---|---|---|
| 58 | 46 | II | P. vivax Treatment Study | Randomized, active-control, double-blind, double-dummy | TQ 400 mg OD for 3 d in Cohort 1 and TQ 600 mg OD for 1 d in Cohort 2 | 120 M/F (60 in each cohort) (20-60 y) | collected at approximately 12 hr and 168 hr after weekly medication and at 14, 21 and 28 d after the last dose. Daily for Days 0-7, Days 12-20 and Days 28-30 | d: days;
F: female;
hr: hours;
M: male;
MQ: mefloquine;
N: number of subjects;
N/A: not available;
No.: number;
OD: once daily;
PK: pharmacokinetic;
SD: standard deviation;
TQ: tafenoquine;
y: years.

TABLE 3

Demographic Summary of Subjects in the Tafenoquine Population PK Analysis

| Baseline Characteristic | Statistic | All Subjects | Male | Female |
|---|---|---|---|---|
| Number of subjects | n (%) | 866 | 808 (93.3) | 58 (6.7) |
| Age (years) | Mean | 27.8 | 27.1 | 37.2 |
|  | SE | 0.28 | 0.25 | 1.68 |
|  | Median | 25.0 | 25.0 | 35.0 |
|  | Min, Max | 18.0, 60.0 | 18.0, 60.0 | 19.0, 60.0 |
| Race |  |  |  |  |
| Asian | n (%) | 181 (20.9) | 172 (19.9) | 9 (1.0) |
| Black or African | n (%) | 26 (3.0) | 21 (2.4) | 5 (0.6) |
| Caucasian/White | n (%) | 626 (72.3) | 582 (67.2) | 44 (5.1) |
| Hispanic | n (%) | 31 (3.6) | 31 (3.6) | — |
| Other | n (%) | 2 (0.2) | 2 (0.2) | — |
| Food |  |  |  |  |
| No | n (%) | 92 (10.6) | 86 (9.9) | 6 (0.7) |
| Yes | n (%) | 774 (89.4) | 722 (83.4) | 52 (6.0) |
| Weight (kg) | Mean | 75.0 | 75.9 | 62.4 |
|  | SE | 0.47 | 0.48 | 1.37 |
|  | Median | 75.0 | 76.0 | 62.3 |
|  | Min, Max | 43.0, 135.0 | 43.0, 135.0 | 43.0, 88.0 | n: number of subjects;
Min: minimum;
Max: maximum;
PK: pharmacokinetic;
SE: standard error.

To summarize the conclusions of this analysis, this analysis demonstrated that a dosing regimen involving an initial dose of 200 mg once per day for three days followed by exposure doses of 200 mg week throughout the period of exposure would result in trough plasma tafenoquine concentrations >80 ng/mL in >95% of individuals. Several alternative dosing regimens that incorporated removal of the initial dose, lowering of the dose given, and monthly administration were also modeled to determine whether they would achieve trough concentrations >80 ng/mL in >50% of individuals. We also modeled two post-exposure prophylaxis regimens to assess the duration of time in which protective plasma tafenoquine concentrations could be maintained. Our results show that an initial dose of 200 mg daily for three days followed by weekly 200 mg exposure doses continued as post-exposure doses until three weeks after potential exposure (e.g., deployment to a malaria area) should offer protection against malaria both throughout the period of exposure and for the period after exposure when latent malarial infections can arise (e.g., three weeks post-exposure).

Methods:

The tafenoquine concentrations of plasma samples across the ten studies were analyzed using a validated high-performance liquid chromatography-mass spectrometry method (HPLC-MS) or HPLC with fluorescence detection as previously described (see, Kocisko D A, Walsh D S, Eamsila C, Edstein M D. Measurement of tafenoquine (WR 238605) in human plasma, and venous and capillary blood by high-pressure liquid chromatography. Ther Drug Monit. 2000; 22:184-189; Charles B G, Miller A K, Nasveld P E, Reid M G, Harris I E, Edstein M D. Population pharmacokinetics of tafenoquine during malaria prophylaxis in healthy subjects. *Antimicrob Agents Chemother.* 2007; 51:2709-2715.

Population PK analyses were carried out using NONMEM version 7.1.2, PDx-Pop version 4.2 (Icon Development Solutions, Hanover, Md.) and Intel Visual Fortran Compiler version 12 on a Microsoft Windows XP platform. Plasma tafenoquine concentrations, demographic information and clinical laboratory results from ten studies were used to build a pooled NONMEM input data file for the current population PK analysis. The data were prepared for analysis using SAS software version 9.1.3 (SAS Institute Inc., Cary, N.C.). Actual dosing and actual blood sampling times, when available, were used for the analysis. Plasma tafenoquine concentrations that were below or equal to the limit of quantification were excluded from the analysis.

Based on the PK profile of tafenoquine from previous modeling efforts (Shanks G D, Oloo A J, Aleman G M, et al. A new primaquine analogue, tafenoquine (WR 238605), for prophylaxis against *Plasmodium falciparum* malaria. Clin Infect Dis. 2001; 33:1968-1974; Obaldia N 3rd, Rossan R N, Cooper R D, et al. WR 238605, chloroquine, and their combinations as blood schizonticides against a chloroquine-resistant strain of *Plasmodium vivax* in *Aotus* monkeys. Am J Trop Med Hyg. 1997; 56:508-10), a one-compartment PK model with first-order absorption and elimination processes was selected to describe best the pharmacokinetics of tafenoquine. As part of the modeling process, a two-compartment PK model with first-order absorption and elimination process was also explored and discarded. The one-compartment PK model was specified in the NONMEM control file and was parameterized in terms of apparent clearance (CL/F), apparent volume of distribution (V/F) and absorption rate constant (Ka) using the PREDPP ADVAN2 with TRANS2 subroutine in NONMEM. First-order conditional estimation (FOCE) with interaction between variance of inter-individual variability and the variance of residual error was used as the estimation method. Inter-individual variability was best described by an exponential error model, as shown below:

$$Pi = \hat{P} \exp(\eta_i)$$

where:
Pi is the estimated parameter for the $i^{th}$ individual.
$\hat{P}$ is the population value for the parameter.
$\eta_i$ are inter-individual random effects for the $i^{th}$ individual for parameter P and were assumed to be independent and symmetrically distributed with a zero mean and a variance $\omega^2$.

Different structural models (additive, proportional, exponential and combined additive and proportional) were investigated for residual unexplained variability (RUV). RUV was best described by a proportional error model, as shown below:

$$C_{ij} = \hat{C}_{ij}(1+\varepsilon_{pij})$$

where:
$C_{ij}$ is the $j^{th}$ observation for the $i^{th}$ individual.
$\hat{C}_{ij}$ is the $j^{th}$ predicted value for the $i^{th}$ individual.
$\varepsilon_{pij}$ is the proportional residual random error for the $i^{th}$ individual and the $j^{th}$ measurement and was assumed to be independent and symmetrically distributed with a zero mean and a variance $\sigma^2$.

For optimal model selection, diagnostic plots were generated by PDx-Pop version 4.2 in conjunction with Microsoft Excel and S+ version 8. The standard criteria of change in the minimum objective function value ($\Delta$OFV) equal to minus twice the log-likelihood of the data as well as diagnostics were used to assess goodness of fit. Successful model runs were determined by each of the following criteria: successful model convergence; a minimum of three significant figures reported for any parameter; a non-singular covariance matrix; completion of the covariance step without warnings; CIs for the structural parameters that did not include zero; absence of trends in the distribution of weighted residuals versus model predictions and in the weighted residuals versus the independent variable; and insensitivity of model convergence and covariance to initial parameter estimates.

Covariate analysis was performed to the base PK model to identify and to evaluate the extent to which the covariates accounted for the variability in the PK parameters. Prior to including covariates in the population model, visual inspection of the relationship between each $\eta$ and covariate was performed using scatter plots. The scatter plots were also used to provide visual identification of collinearity between the covariates of interest. Covariates that were identified to demonstrate collinearity based on exploratory plots were not allowed to enter the covariate model at the same time. The decision to include covariates in the final model was also based on whether it was sensible physiologically to include them.

Sex, age, race and body weight (WT) were selected for evaluation as potential covariates of CL/F, V/F and Ka. Starting with the base PK model, a process was initiated in which covariates were selected one at a time and included in the model if inclusion resulted in a reduction in the OFV of at least 3.84 ($p \leq 0.05$, df=1). This process was followed by a multivariate analysis, in which all selected covariates were added together and the model was fit to the data, resulting in the full PK model. Backward deletion was applied by dropping one covariate at a time until no covariate could be removed without significantly increasing the OFV ($p \leq 0.001$), resulting in the final PK model. However, if a CI of any of the covariate effects included the null value, the effect was considered not significant and the model was further simplified until all structural parameters were well estimated. Continuous covariates in the model were centered on the population median value of the subjects included in the analysis and are described in more detail in the results section.

The final PK model was evaluated using bootstrapping and a visual predictive check. Using the bootstrap approach, the bootstrap parameter values were obtained by repeatedly fitting the final population model to 1000 bootstrap samples. The mean and CI values of the bootstrap parameters were then compared to the final population model parameter estimates and associated CIs from NONMEM. The 95% bootstrap percentile CIs were determined for the PK parameters derived from 1000 bootstrap datasets and compared to the original parameters obtained from the final model.

A visual predictive check was performed by simulating the plasma tafenoquine concentrations from the original subjects in the NONMEM dataset using the parameter estimates from the final PK model. One thousand predicted profiles were simulated for each original subject. Random effects were included in the simulation. The median, $5^{th}$ percentile and $95^{th}$ percentile PK concentration-versus-time profiles from the simulations were compared with those from observed plasma tafenoquine concentrations.

Simulations of PK data for various doses and dose regimens were performed using the final PK model parameters. The simulation step included creation of NONMEM data files with virtual subjects with desired sampling times and dosing regimens and running of the simulations with 2000 replicates using the final PK model parameters in NONMEM. The outputs from the simulations were summarized using SAS software version 9.1.3 and presented graphically using Phoenix WinNonlin version 6.2 (Pharsight, St. Louis, Mo.).

A one-compartment PK model with first-order absorption and elimination rate constants was selected as the structural model. Different error models for inter-individual and residual unexplained variability were also tested. The exponential error model was chosen to describe inter-individual variability of each PK parameter (CL/F, V/F and Ka) and the proportional error model was chosen to describe residual error. A two-compartment PK model was also tested but was not pursued further because of unreliable estimates from bootstrap results during model evaluation (data not shown).

Because age, WT, race, sex and meal condition (fed versus fasted) were the only common covariates present for all ten studies, these covariates were selected for covariate model exploration. Each of these covariates was included in the base PK model to test for its significance. Because diversity in race was restricted due to a majority of the subjects being Asian or Caucasian, the effect of race was explored only for Asian subjects versus Caucasian/other subjects as the reference. Sex and race were confounded with WT and were not explored further in the full covariate model.

Figure 1:
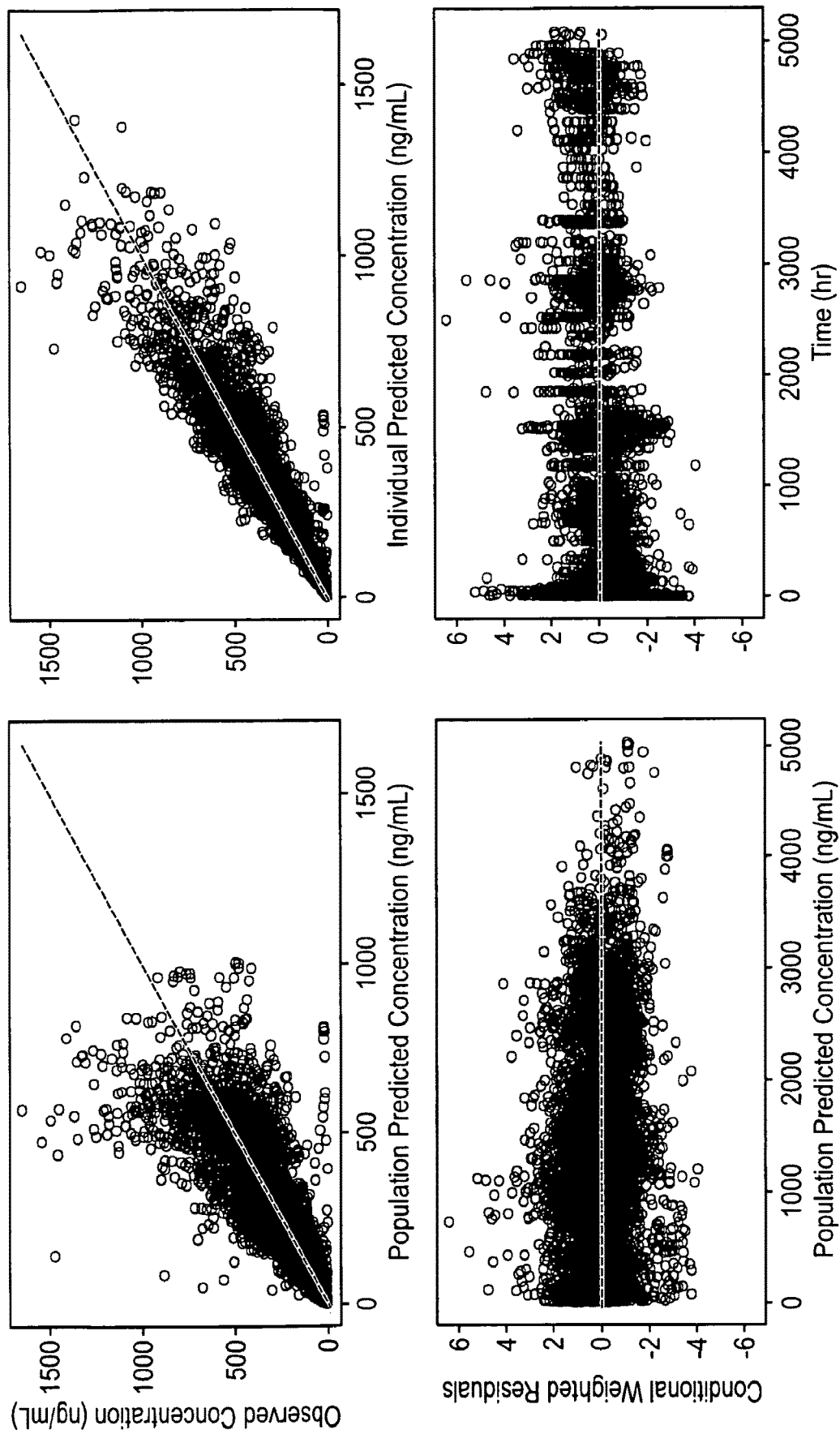
FIG. 1 Goodness-of-fit plots of plasma tafenoquine concentrations for the final pharmacokinetic model. The solid line represents the line of identity.

The full covariate model included the effect of WT on CL/F and V/F; age on CL/F, V/F and Ka; and meal condition on V/F and Ka. The effect of meal condition on bioavailability alone could not be explored and the effect of meal condition on CL/F was not significant. The full covariate PK model was further reduced by backward elimination and resulted in WT and age as significant covariates of CL/F, and WT and meal condition as significant covariates of V/F. Goodness-of-fit plots are presented in FIG. 1 and support that the model fit available concentration data.

Base structural parameters and the relationship of covariates to CL/F and V/F are summarized in Table 4. For oral tafenoquine, the population CL/F and V/F were determined to be 4.17 L/h and 2470 L, respectively. The first-order Ka of oral tafenoquine was 0.359 The inter-individual variability of CL/F, V/F and Ka was 23.6%, 24.1% and 54.1%, respectively. The final PK model revealed that CL/F of tafenoquine is a function of WT and age. These covariates decreased inter-individual variability associated with CL/F from 26.5% to 23.6%. The relationship between CL/F and both covariates was as follows:

$$CL/F(L/h)=4.17\times(WT/75)^{0.552}\times(AGE/25)^{-0.2}$$

TABLE 4

Tafenoquine Population PK Parameters of the Final PK Model

| Parameters (Units) | Final Estimate | Bootstrap 95% CI Lower | Bootstrap 95% CI Upper | Inter-individual Variability a |
|---|---|---|---|---|
| CL/F (L/h) = $\theta_{CL}\times(WT/75)^{\theta_{CL-WT}}\times(AGE/25)^{\theta_{CL-AGE}}$ | | | | |
| $\theta CL$ | 4.17 | 4.080 | 4.230 | 23.6% |
| $\theta CL-WT$ | 0.552 | 0.474 | 0.637 | |
| $\theta CL-AGE$ | −0.200 | −0.267 | −0.138 | |
| V/F (L) = $\theta_V\times(WT/75)^{\theta_{V-WT}}\times(\theta_{V-FOOD})^{FOOD}$ | | | | |
| $\theta V$ | 2470 | 2340 | 2630 | 24.1% |
| $\theta V-WT$ | 0.781 | 0.652 | 0.901 | |
| $\theta V-FOOD$ | 0.822 | 0.761 | 0.861 | |
| Ka (1/h) | 0.359 | 0.321 | 0.384 | 54.1% |
| $\omega^2 CL$ | 0.0555 | 0.0462 | 0.0618 | |
| $COV_{CL,V}$ | 0.0289 | 0.0186 | 0.0315 | |
| $\omega^2 V$ | 0.0583 | 0.0444 | 0.0606 | |
| $\omega^2 Ka$ | 0.293 | 0.203 | 0.378 | |
| $\sigma^2$ | 0.0488 | 0.0436 | 0.0553 | |

CL or CL/F: apparent clearance;
CI: confidence interval;
COV: covariance;
hr: hours;
Ka: absorption rate constant;
PK: pharmacokinetic;
V or V/F: apparent volume of distribution;
WT: weight;
$\omega^2$: variance of the inter-individual random effect;
$\sigma^2$: variance of the proportional residual random effect.
[a]The magnitude of inter-individual variability was presented as the coefficient of variation.
Note:
Final estimate and inter-individual variability were from NONMEM estimates.
FOOD = 0 for fasted and 1 for fed.

Thus, tafenoquine CL/F was found to increase as WT increased (expressed in kilograms) and to decrease with age (expressed in years).

The final PK model revealed that V/F of tafenoquine is a function of WT and meal condition. These covariates decreased the inter-individual variability of V/F from 29.6% to 24.1%. The relationship between V/F and both covariates was as follows:

$$V/F(L)=2470\times(WT/75)^{0.781}\times(0.822)^{FOOD}$$

where FOOD=0 for fasted and 1 for fed.

Tafenoquine V/F was found to increase as WT increased and to decrease in the fed condition compared with the fasting condition.

The bootstrapping technique was used to evaluate the final PK model. The comparison between the parameter estimates derived from the bootstrap and the estimates derived from NONMEM and between the estimates of the variability of the random effects derived from the bootstrap and the corresponding NONMEM estimates are presented in Table 5. In this modeling effort, the differences of mean bootstrap estimates from the NONMEM estimates of those parameters were less than 15%. Overall, the mean population PK parameter estimates and 95% CI obtained from the bootstrap procedure were comparable to the estimates and 95% CI from the final PK model. The success rate of bootstrap runs was 100% for the PK model.

TABLE 5

Comparison of Bootstrap and NONMEM Parameter Estimates for Tafenoquine

| Parameters | NONMEM Estimate | Bootstrap Estimate | Difference[a] |
|---|---|---|---|
| $\theta CL$ | 4.17 | 4.15 | −0.37% |
| $\theta CL-WT$ | 0.552 | 0.554 | 0.35% |
| $\theta CL-AGE$ | −0.200 | −0.200 | 0.08% |
| $\theta V$ | 2470 | 2482 | 0.47% |
| $\theta V-WT$ | 0.781 | 0.774 | −0.96% |
| $\theta V-FOOD$ | 0.822 | 0.810 | −1.52% |
| $\theta KA$ | 0.359 | 0.351 | −2.29% |
| $\omega^2 CL$ | 0.0555 | 0.0536 | −3.44% |
| $COV_{CL,V}$ | 0.0289 | 0.0250 | −13.40% |
| $\omega^2 V$ | 0.0583 | 0.0521 | −10.55% |
| $\omega^2 Ka$ | 0.293 | 0.283 | −3.49% |
| $\sigma^2$ | 0.0488 | 0.0486 | −0.50% |

CL or CL/F: apparent clearance;
COV: covariance;
Ka: absorption rate constant;
PK: pharmacokinetic;
V or V/F: apparent volume of distribution;
WT: weight;
$\omega^2$: variance of the inter-individual random effect;
$\sigma^2$: variance of the proportional residual random effect.
[a]Expressed as percent of difference between bootstrap and NONMEM estimates from the final model ([Bootstrap/NONMEM − 1] × 100%).

Figure 2:
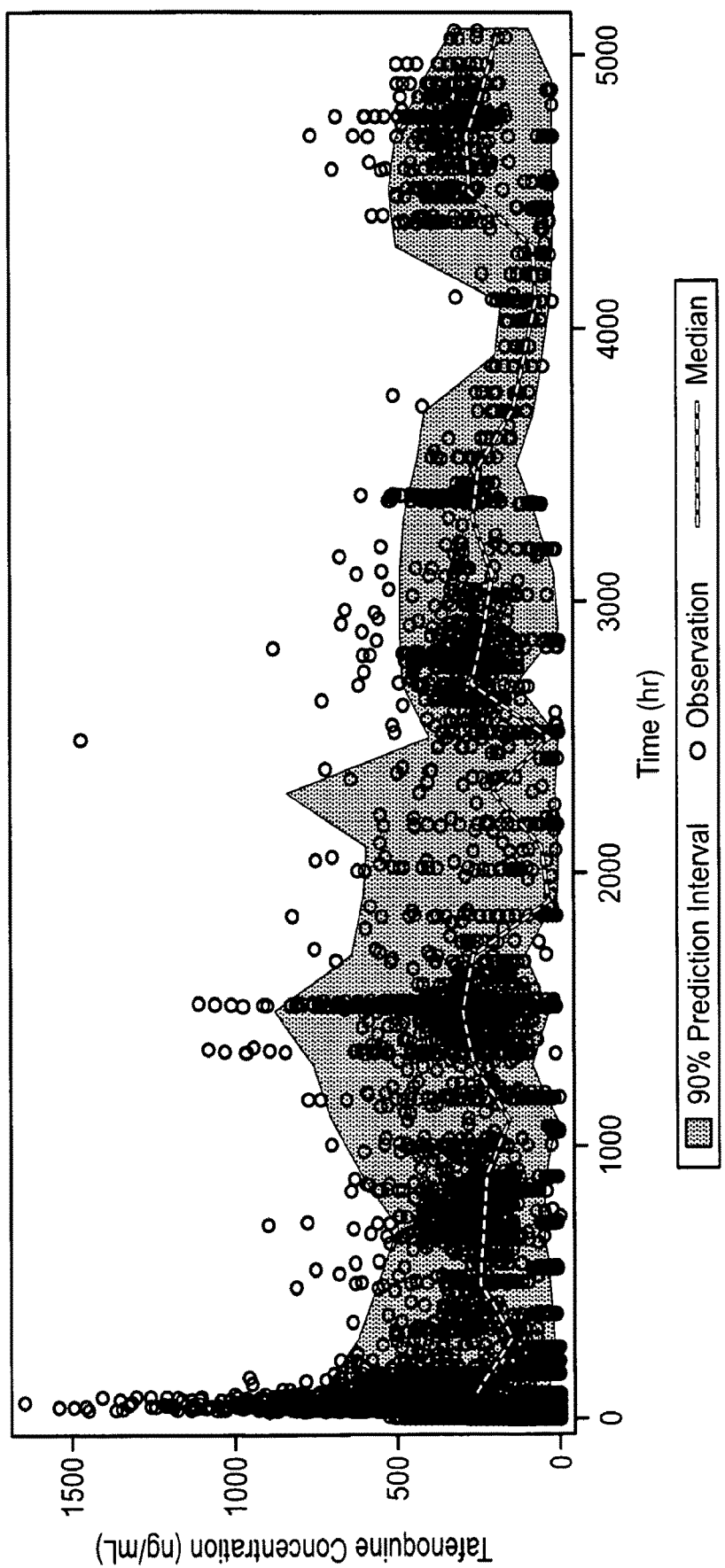
FIG. 2 Visual predictive check of model-predicted vs. observed plasma concentrations of tafenoquine.

The visual predictive check was performed using the NONMEM parameter estimates estimated from the final PK model. Median, 5th percentile and 95th percentile plots of model-predicted versus observed plasma tafenoquine concentrations are presented in FIG. 2. The results demonstrate the adequacy of the final PK model to reproduce a majority of plasma tafenoquine concentrations over the course of several dose levels. 90.56% of the observations were within the 90% prediction interval (4.90% were below the 5th percentile and 4.55% were higher than the 95th percentile).

Figure 4:
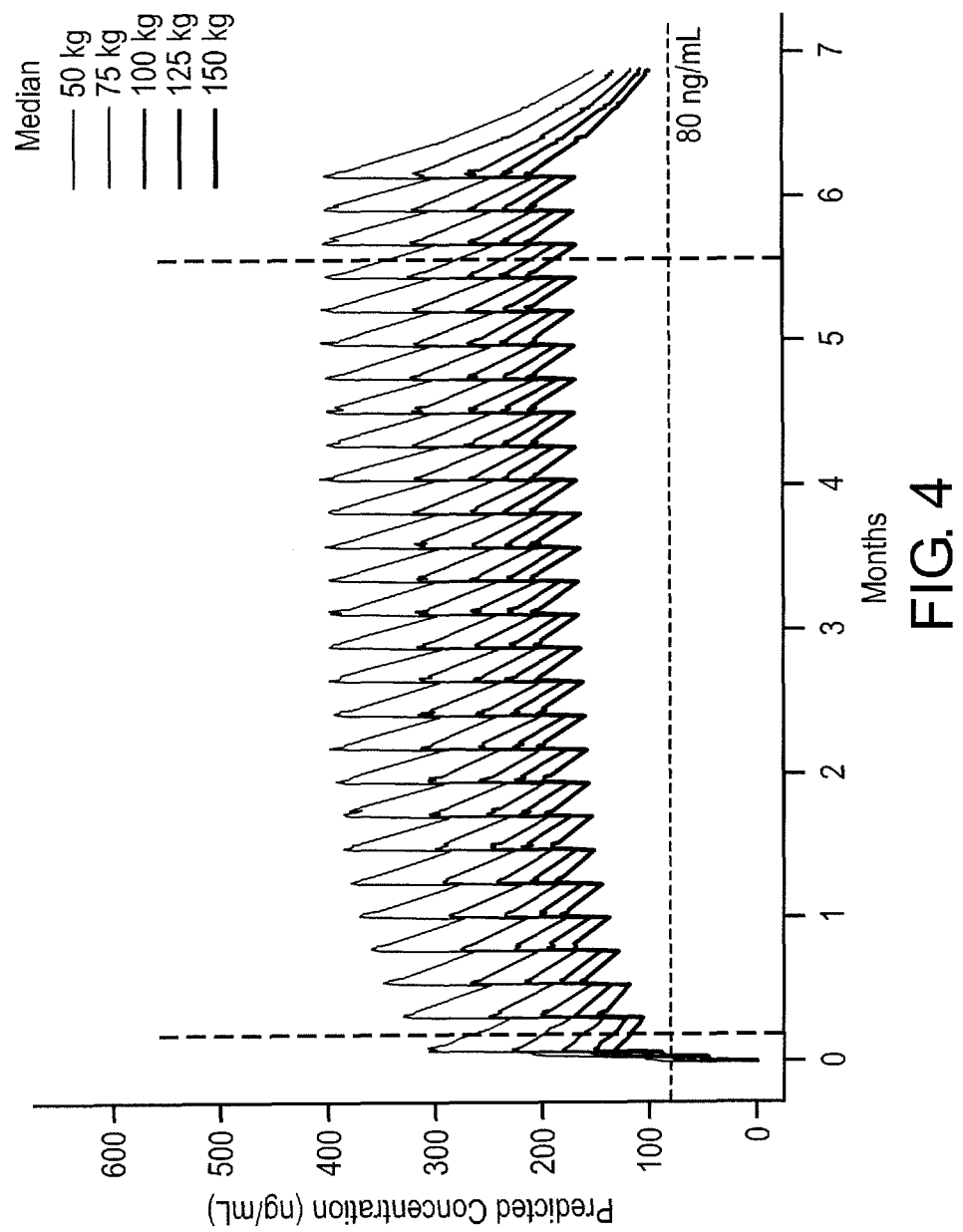
FIG. 4 Tafenoquine plasma concentration-time profiles (median) for the Reference Regimen at different body weights. The Reference Regimen consists of initial doses of 200 mg once daily for three days prior to exposure, followed by exposure doses of 200 mg once per week during exposure, and post-exposure doses 200 mg once per week for three weeks post-exposure. The hashed horizontal line represents the 80 ng/mL concentration threshold. The left hashed vertical line represents when deployment and exposure doses begin. The period of time prior to the left hashed vertical line indicates the time during which initial doses are given. The right hashed vertical line represents when deployment ends and post-exposure dosing beings. Each peak represents the maximum concentration following administration of each new dose. This shows that the reference regimen is protective at different body weights because the median concentrations are always higher than the protective threshold concentrations.
Figure 5:
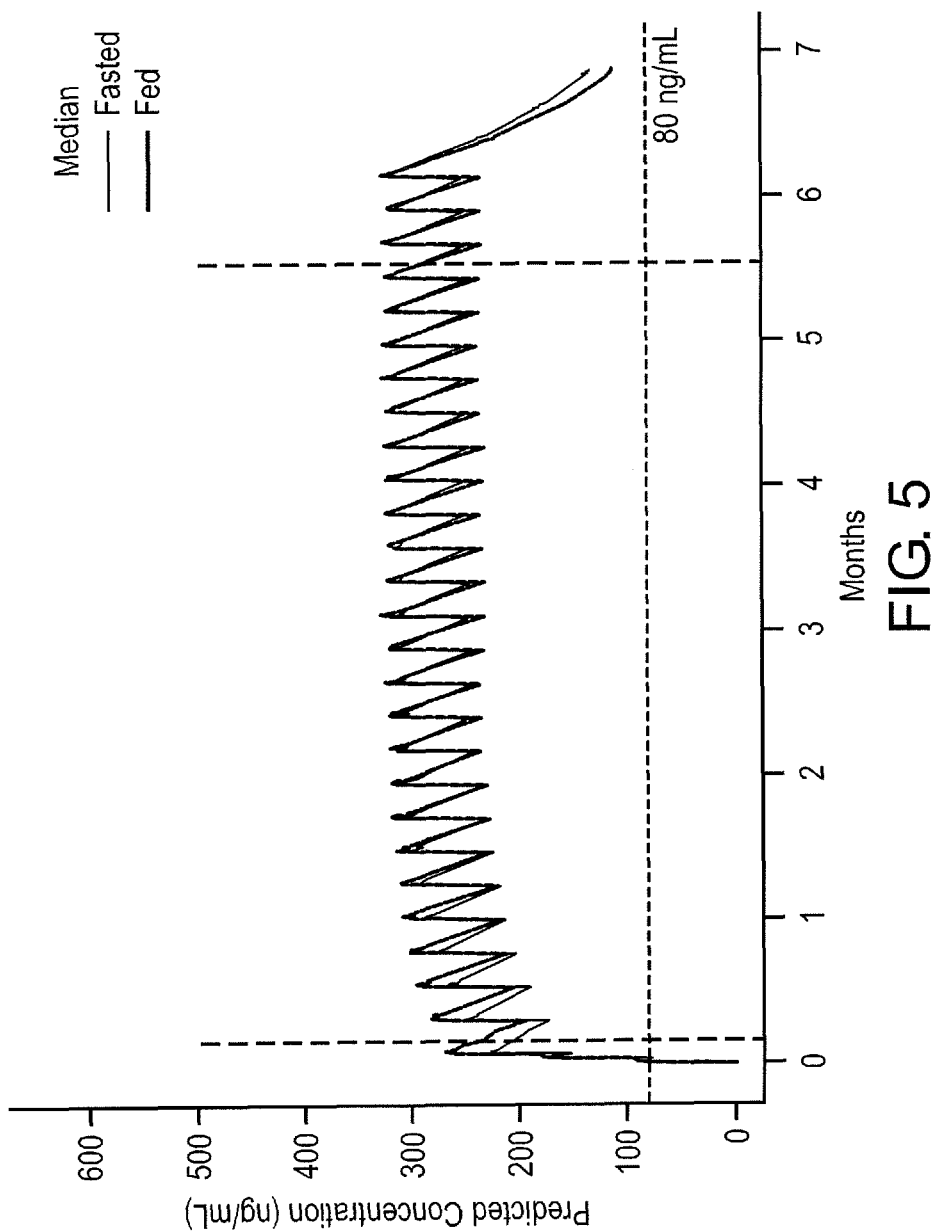
FIG. 5 Tafenoquine plasma concentration-time profiles (median) for the Reference Regimen in fed and fasted individuals. The Reference Regimen consists of initial doses of 200 mg once daily for three days prior to exposure, followed by exposure doses of 200 mg once per week during exposure, and post-exposure doses 200 mg once per week for three weeks post-exposure. The hashed horizontal line represents the 80 ng/mL concentration threshold. The left hashed vertical line represents when deployment and exposure doses begin. The period of time prior to the left hashed vertical line indicates the time during which initial doses are given. The right hashed vertical line represents when deployment ends and post-exposure dosing beings. Each peak represents the maximum concentration following administration of each new dose. This shows that the Reference Regimen is effective either in the fed or the fasted state, because median drug concentrations are higher the 80 ng/ml protective threshold.
Figure 6:
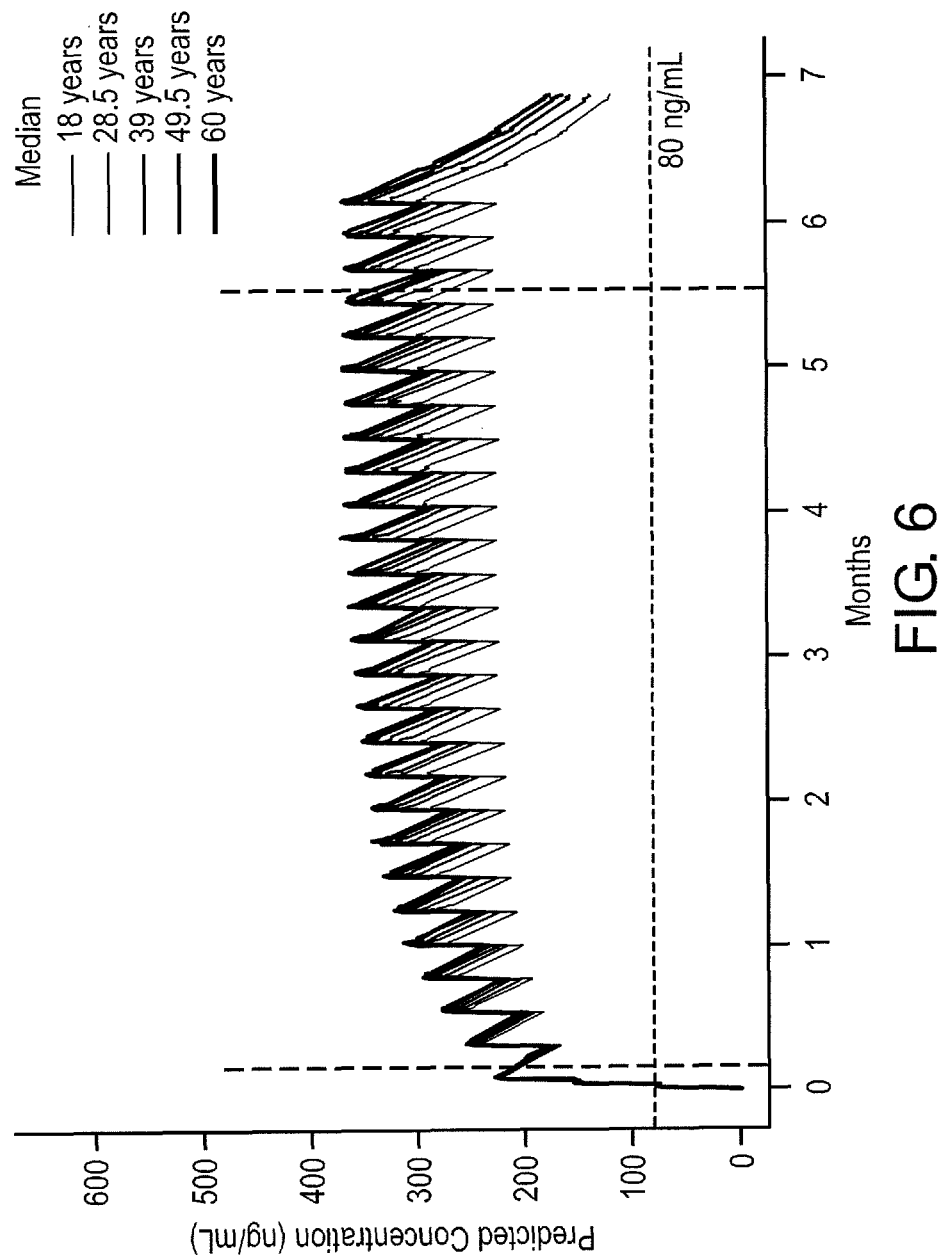
FIG. 6 Tafenoquine plasma concentration-time profiles (median) of the Reference Regimen in individuals of different ages. The Reference Regimen consists of initial doses of 200 mg once daily for three days prior to exposure, followed by exposure doses of 200 mg once per week during exposure, and post-exposure doses 200 mg once per week for three weeks post-exposure. The hashed horizontal line represents the 80 ng/mL concentration threshold. The left hashed vertical line represent when deployment and exposure doses begin. The period of time prior to the left hashed vertical line indicates the time during which initial doses are given. The right hashed vertical line represents when deployment ends and post-exposure dosing beings. Each peak represents the maximum concentration following administration of each new dose. This shows that the Reference Regimen is effective across different age ranges because the median concentrations are always higher the 80 ng/ml protective threshold during deployment.

Results:

The simulated reference regimen (200 mg daily for three days then 200 mg weekly) resulted in the achievement of plasma tafenoquine concentrations >80 ng/mL immediately after the loading dose in 95% of individuals (FIG. 3). Concentrations decreased below this threshold briefly in more than 5% of Australian soldiers at the first trough but remained above 80 ng/mL throughout the remainder of the simulated six-month deployment in 95% of individuals (FIG. 3). Median tafenoquine steady-state trough plasma concentrations after simulation of the reference regimen decreased as WT increased but were predicted to remain higher than the desired threshold in the majority of individuals at all levels of body weight (FIG. 4). After administration of the reference regimen in the fed meal condition, plasma tafenoquine concentrations were increased prior to the attainment of steady-state; however, this increase was expected to have a minimal impact on plasma tafenoquine concentrations at steady-state (FIG. 4). Plasma tafenoquine concentrations at steady-state following the administration of the reference regimen were expected to increase with an increase in age (FIG. 5), and this increased concentration was most likely due to the effect of age on CL/F. However, steady state concentrations were higher in the majority of individuals at all ages.

Variations of the Reference Regimen are simulated in FIG. 7. In simulations in which the initial dose component of the intended regimen was removed (Compare Regimen 1), and/or or the dose was lowered to 100 or 150 mg (Regimens 2 and 6) median trough plasma tafenoquine concentrations exceeded the intended 80 ng/mL after two or three weekly doses. Simulation of the prophylactic monthly regimen utilized in Thai marines (Regimen 4, FIG. 7) predicted that median steady-state trough plasma tafenoquine concentrations >80 ng/mL did not persist for the entire simulated deployment (FIG. 7) and were lower than those of the Reference Regimen, and Regimens 1, 2 and 6 (compare FIGS. 3 and 7). In the simulation in which 50 mg was given weekly with no loading dose (Regimen 7), median steady state trough concentrations never exceeded the intended threshold.

Upon return from a malaria endemic area, it is usual practice to administer a regimen for post-exposure prophylaxis to reduce the risk of contracting *P. falciparum* malaria in the final three weeks of deployment and to prevent *P. vivax* relapses. Simulation of the administration of a post-exposure prophylaxis regimen of 200 mg once daily for three days (Regimen 3, FIG. 7) or 200 mg once weekly for three weeks (extended Reference Regimen, FIG. 8) predicted that plasma tafenoquine concentrations >80 ng/mL will be maintained for greater than one month (FIGS. 7 and 8). In addition, the peak plasma concentration (C max) of tafenoquine after administration of Regimen 3 (i.e., following a reverse load of 200 mg daily for three days) was predicted to be lower than that attained after administration of the loading dose of 400 mg daily for three days employed both in Thai marines (Llanos-Cuentas A, Lacerda M V, Rueangweerayut R, et al. Tafenoquine plus chloroquine for the treatment and relapse prevention of *Plasmodium vivax* malaria (DETECTIVE): a multicentre, double-blind, randomised, phase 2b dose-selection study. *Lancet.* 2014; 383: 1049-1058) and in semi-immune residents of Kenya (Li Q, O'Neil M, Xie L, et al. Assessment of the prophylactic activity and pharmacokinetic profile of oral tafenoquine compared to primaquine for inhibition of liver stage malaria infections. *Malar J.* 2014; 13:141) (Regimen 4, FIG. 7), see FIG. 7 for full profile and compare FIGS. 3 and 8 for concentrations after the last dose).

A total of 866 subjects were included in this population PK modeling of tafenoquine. Results showed that a one-compartment PK model with first-order absorption and elimination was an appropriate base PK model for describing the pharmacokinetics of tafenoquine administered orally. Inter-individual variability was described by an exponential model and residual variability was described by a proportional model. Model evaluation using bootstrapping and the visual predictive check confirmed the reliability of the final PK model and its reproduction of plasma tafenoquine concentrations.

Variability in the final PK model was explained by the effect of changes in WT and age on CL/F, and WT and meal status on V/F although assessment of the effect of meal status on V/F was limited by the relatively small percentage of subjects dosed under fasted conditions. The explained variability is not sufficient to suggest that the intended regimen should be modified based on either age or meal status in order to achieve the desired steady-state plasma tafenoquine concentration, because the reference regimen is predicted to result in the attainment of the intended steady-state trough plasma tafenoquine concentrations in >95% of individuals. The effect of WT, age and meal status are evident, but even in these sub-populations, protective plasma tafenoquine concentrations are achieved in the vast majority of individuals.

The data shows that removal of the loading dose and/or lowering the dose to 100 or 150 mg would result in the attainment of protective plasma tafenoquine concentrations over the entirety of the simulated deployment of six months. Protective concentrations would be reached with all these regimens after the second or third dose. A monthly dosing schedule is predicted not to result in the attainment of protective plasma tafenoquine concentrations over the entirety of the simulated deployment of six months, confirming clinical experience with this regimen in Thai marines (Edstein M D, Kocisko D A, Walsh D S, Eamsila C, Charles B G, Rieckmann K H. Plasma concentrations of tafenoquine, a new long-acting antimalarial agent, in Thai soldiers receiving monthly prophylaxis. *Clin Infect Dis.* 2003; 37:1654-1658).

As highlighted in a recent retrospective analysis of the efficacy of tafenoquine in non-immune subjects (Dow G S, Mc Carthy W F, Reid M, Smith B, Tang D, Shanks D G. A retrospective analysis of the protective efficacy of tafenoquine and mefloquine as prophylactic anti-malarials in non-immune individuals during deployment to a malaria-endemic area. *Malaria Journal.* 2014, 13:49), a post-dosing regimen may be needed to manage the residual risk of malaria from later exposure during travel. We explored two post-exposure prophylaxis regimens of tafenoquine: administration of a reverse load of 200 mg once daily for three days (Regimen 3) versus extension of the reference regimen for an additional three weeks. The extended reference regimen maintained trough plasma tafenoquine concentrations >80 ng/mL for approximately three to four days longer in 95% of individuals than did the reverse load, but tafenoquine concentrations of both regimens remained in excess of the threshold in a majority of individuals for at least one month. The C max of tafenoquine achieved after administration of the reverse load was lower than that attained after administration of 400 mg once daily for three days. A loading dose of 400 mg once daily for three days has been shown to be safe in G6PD-normal individuals in several clinical studies but exhibits gastrointestinal intolerability (Shanks G D, Oloo A J, Aleman G M, et al. A new primaquine analogue, tafenoquine (WR 238605), for prophylaxis against *Plasmodium falciparum* malaria. *Clin Infect Dis.* 2001; 33:1968-1974; Walsh D S, Eamsila C, Sasiprapha T, et al. Efficacy of monthly tafenoquine for prophylaxis of *Plasmodium vivax* and multidrug-resistant *P. falciparum* malaria. *J Infect Dis.* 2004; 190:1456-1463; Elmes N J, Nasveld P E, Kitchener S J, Kocisko D A, Edstein M D. The efficacy and tolerability of three different regimens of tafenoquine versus primaquine for post-exposure prophylaxis of *Plasmodium vivax* malaria in the Southwest Pacific. *Trans R Soc Trop Med Hyg.* 2008; 102:1095-1101). The incidence of gastrointestinal adverse events after the administration of 200 mg tafenoquine once daily for three days (total dose 600 mg) is approximately half of that after administration of 400 mg once daily or BID for three days (total dose 1200 mg) and similar to the standard of care (Elmes N J, Nasveld P E, Kitchener S J, Kocisko D A, Edstein M D. The efficacy and tolerability of three different regimens of tafenoquine versus primaquine for post-exposure prophylaxis of *Plasmodium vivax* malaria in the Southwest Pacific. *Trans R Soc Trop Med Hyg.* 2008; 102:1095-1101). It is therefore conceivable that gastrointestinal intolerability might be no worse than the standard of care for those who receive the reverse load (200 mg once daily for three days). However, additional clinical data are required to demonstrate this directly.

Recent reports have associated *P. vivax* relapses/primaquine failures with polymorphisms in cytochrome P450 (CYP) 2D6 (Bennett J W, Pybus B S, Yadava A, et al. Primaquine failure and cytochrome P-450 2D6 in *Plasmodium vivax* malaria. *N Engl J Med* 2013; 369:1381-1382). Presumably, this is because the production of an unknown primaquine metabolite that is important for *P. vivax* antihypnozoite activity is inhibited in individuals with CYP2D6 mutations. Conceivably, the same might also be true for tafenoquine. If so, it likely has no clinical relevance in the context of prophylactic use. This is because at the reference regimen described here, no malaria breakthroughs were observed in a large cohort of non-immune and primarily Caucasian Australian soldiers (Bennett J W, Pybus B S, Yadava A, et al. Primaquine failure and cytochrome P-450 2D6 in *Plasmodium vivax* malaria. *N Engl J Med* 2013; 369:1381-1382). Although CPY2D6 polymorphisms were not determined in the 491 Australian soldiers who received tafenoquine, a good number would have been poor metabolizers, because the prevalence of CYP2D6 poor metabolizers in Caucasian populations ranges from 6% to 10% (*Australian Medicines Handbook* 2004. Adelaide: Australian Medicines Handbook Pty Ltd; 2004).

The Australian and U.S. Armed Forces routinely use daily doxycycline or atovaquone/proguanil for malaria prophylaxis (DOD Health Memo: http://www.health.mil/~/media/MHS/Policy %20Files/Import/13-002.ashx; Shanks G D, Mines N J. Malaria in the military and Melanesia. *ADF Health,* 2008; 9:54-59). Weekly mefloquine is used where the risk-benefit is appropriate (DOD Health Memo: http://www.health.mil/~/media/MHS/Policy %20Files/Import/13-002.ashx). Post-exposure prophylaxis usually involves administration of a blood-schizonticidal anti-malarial for one month (doxycycline or mefloquine), a causal prophylactic drug for seven days (atovaquone/proguanil) and/or a combination of a blood-schizonticidal drug (doxycycline) and primaquine for two weeks to reduce the risk of *P. vivax* relapse or the contraction of *P. falciparum* malaria from late-deployment exposure (DOD Health Memo: http://www.health.mil/~/media/MHS/Policy %20Files/Import/13-002.ashx; Shanks G D, Elmes N J. Malaria in the military and Melanesia. *ADF Health.* 2008; 9:54-59). Weekly tafenoquine extended for three weeks following deployment is predicted to maintain the same level of protection as the standard of care and provide a more convenient prophylaxis and post-exposure prophylaxis regimen. Compression of the post-exposure prophylactic regimen to a three-day reverse load (200 mg/day or lower daily dose for 3 days) could further economize the dosing schedule, and thus improve compliance, but additional clinical data are required to assess GI tolerability. There will remain a small risk of *P. vivax* relapses, but this risk is not anticipated to be greater than that of the standard of care (blood schizontocide plus primaquine 30 mg/day for 14 days) (Elmes N J, Nasveld P E, Kitchener S J, Kocisko D A, Edstein M D. The efficacy and tolerability of three different regimens of tafenoquine versus primaquine for post-exposure prophylaxis of *Plasmodium vivax* malaria in the Southwest Pacific. *Trans R Soc Trop Med Hyg.* 2008; 102:1095-1101).

In Example 1, the population pharmacokinetics of tafenoquine were assessed using data from ten Phase I/II/III clinical studies, resulting in a stable, predictive model used to confirm the efficacy of the intended reference tafenoquine regimen (200 mg/day for 3 days, then 200 mg weekly) and to explore additional regimens. Elimination of the loading dose and/or reduction of the dose to 100 and 150 mg maintained protective levels of drug in the majority of individuals. Two additional post-exposure prophylaxis regimens (Regimen 3 reverse load of 200 mg/day for 3 days and the extended reference regimen) showed promise for being well tolerated and effective. Tafenoquine administered weekly for three weeks following deployment is predicted to maintain the same level of protection as the standard of care and provide a more convenient prophylaxis and post-exposure prophylaxis regimen. Compression of the post-exposure prophylactic regimen to a three-day reverse load (Regimen 3) could further economize the dosing schedule. A small risk of *P. vivax* relapse will remain but is not anticipated to be greater than that of the standard of care.

REFERENCES

1. Brueckner R P, Coster T, Wesche D L, Shmuklarsky M, Schuster B G. Prophylaxis of *Plasmodium falciparum* infection in a human challenge model with WR 238605, a new 8-aminoquinoline antimalarial. *Antimicrob Agents Chemother.* 1998; 42:1293-1294.
2. Marcsisin S R, Sousa J C, Reichard G A, et al. Tafenoquine and NPC-1161B require CYP 2D metabolism for anti-malarial activity: implications for the 8-aminoquinoline class of anti-malarial compounds. *Malar J* 2014; 13:2.
3. Idowu O R, Peggins J O, Brewer T G, Kelley C. Metabolism of a candidate 8-aminoquinoline antimalarial agent, WR 238605, by rat liver microsomes. *Drug Metab Dispos.* 1995; 23:1-17.
4. Lobel H O, Bernard K W, Williams S L, Hightower A W, Patchen L C, Campbell C C. Effectiveness and tolerance of long-term malaria prophylaxis with mefloquine. Need for a better dosing regimen. *JAMA.* 1991; 26:361-364.
5. Lobel H O, Miani M, Eng T, Bernard K W, Hightower A W, Campbell C C. Long-term malaria prophylaxis with weekly mefloquine. *Lancet.* 1993; 341:848-851.
6. Food and Drug Administration Guidance for Industry. Exposure-Response Relationships—Study Design, Data Analysis, and Regulatory Applications. 2003.

The teachings of all patents, published applications, and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of prevention of symptomatic *P. falciparum* malaria in a human subject, comprising:

a) administering to the human subject two or more initial doses of a compound of Formula (I), a pharmaceutically acceptable salt thereof, or a pharmaceutical composition comprising a compound of Formula (I), wherein at least the first initial dose is administered prior to potential exposure of the subject to *P. falciparum*; and b) administering to the human subject an exposure dose of said compound or composition one or more times per week during potential exposure of the subject to *P. falciparum*;

wherein about 75 to about 299 mg of said compound of Formula (I) is administered in each of said two or more initial doses, wherein the total combined amount of said compound of Formula (I) administered in said initial doses is about 500 mg to about 900 mg, wherein the total amount of said compound of Formula (I) administered through said exposure dose(s) is about 75 to about 299 mg per week, wherein the human subject is malaria-nave and Glucose-6-phosphate dehydrogenase (G6PD) normal, and wherein Formula (I) has the following structure,

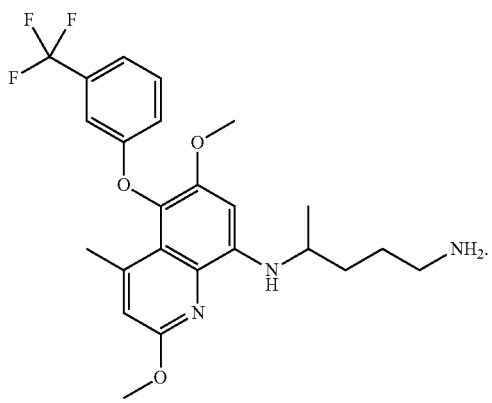 [SMILES: COc1cc(C)c2c(Oc3cccc(C(F)(F)F)c3)c(OC)cc(NC(C)CCCN)c2n1]

2. The method of claim 1, wherein the initial dose is administered once per day for three days.

3. The method of claim 1, wherein the exposure dose(s) are administered once per week.

4. The method of claim 1, wherein the initial dose is administered three or four times.

5. The method of claim 1, wherein the exposure dose is administered once per day.

6. The method of claim 1, wherein the exposure dose is administered one to seven times per week.

7. The method of claim 1, wherein the administration is sufficient to produce a C min serum or plasma concentration of at least about 80 ng/mL of said compound of Formula (I) prior to potential exposure to *P. falciparum* and to substantially maintain that serum or plasma concentration throughout to *P. falciparum* in more than 50% of individuals administered the given initial and exposure doses.

8. The method of claim 1, wherein the administration is sufficient to produce a C min serum or plasma concentration of at least about 80 ng/mL of the compound of Formula (I) prior to potential exposure to *P. falciparum* and to substantially maintain that serum or plasma concentration throughout potential exposure to *P. falciparum* in 95% or more of a population of subjects administered the given initial and exposure doses.

9. The method of claim 1, wherein the human subject is an adult.

10. The method of claim 1, wherein the human subject is a child.

11. The method of claim 1, wherein the compound, the salt, or the pharmaceutical composition is administered orally or sublingually.

12. The method of claim 1, wherein the pharmaceutically acceptable salt of a compound of Formula (I) is tafenoquine succinate.

13. The method of claim 1, wherein the pharmaceutically acceptable salt of a compound of Formula (I) is a salt of tafenoquine or a salt having the following structure,

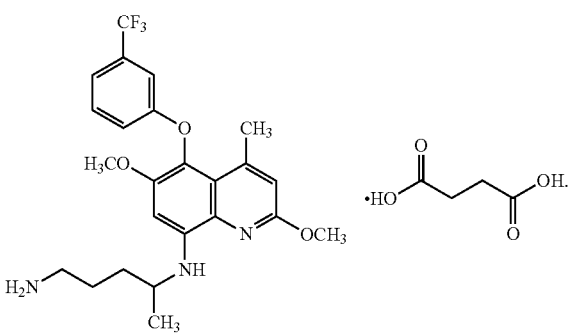

14. The method of claim 1, further comprising administering to the human subject one or more post-exposure dose(s) of a compound of Formula (I), a pharmaceutically acceptable salt thereof, or a pharmaceutical composition comprising a compound of Formula (I), within 1-10 days after the risk of continued exposure to *P. falciparum* has substantially ended, wherein each said post-exposure dose comprises 40 mg to about 399 mg of the compound of Formula (I).

15. The method of claim 14, wherein the post-exposure dose is administered one to three times.

16. The method of claim 1, wherein a C min serum or plasma concentration of at least about 80 ng/mL of the compound of Formula (I) is obtained prior to potential exposure to *P. falciparum* and is substantially maintained throughout potential exposure to *P. falciparum* in the human subject.

17. A kit comprising:

a) one or more initial dose(s) of about 75 to about 299 mg of a compound of Formula (I), a pharmaceutically acceptable salt thereof, or a pharmaceutical composition comprising a compound of Formula (I);

b) a plurality of exposure doses of the compound, salt, or composition, wherein the total administered amount of the exposure dose is about 75 to 299 mg per week of the compound of Formula (I);

c) instructions for taking said one or more initial dose(s), wherein at least the first initial dose is taken prior to potential exposure of the subject to *P. falciparum*, and for taking said exposure doses one or more times per week during potential exposure of the subject to *P. falciparum*, wherein Formula (I) has the following structure,

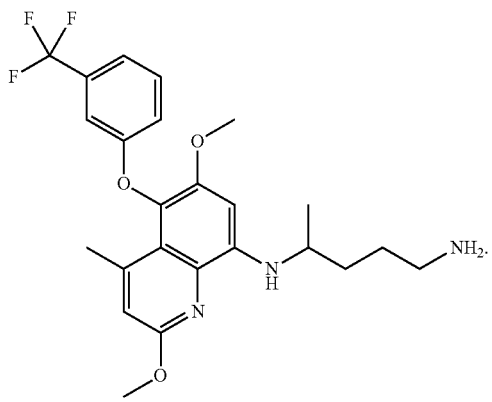 [SMILES: COc1cc(C)c2c(Oc3cccc(C(F)(F)F)c3)c(OC)cc(NC(C)CCCN)c2n1]

18. The kit of claim 17, further comprising:
    d) one or more post-exposure dose(s) of about 40 to about 399 mg of the compound of Formula (I);
    wherein said instructions include taking said post-exposure dose(s) one or more times after potential exposure of the subject to *P. falciparum*.

19. The method of claim 1, wherein the initial doses is about 200 mg and administered once a day for three days, and
    wherein the exposure doses is about 200 mg and is administered once a week.

20. The method of claim 19, wherein the first exposure dose is administered seven days after the third initial dose.

21. The method of claim 14, wherein the initial doses is about 200 mg and administered once a day for three days,
    wherein the exposure doses is about 200 mg and is administered once a week, and wherein the post-exposure dose is administered once.

22. The method of claim 21, wherein the first exposure dose is administered seven days after the third initial dose, and wherein the post-exposure dose is administered seven days after the last exposure dose.

23. A method of prevention of symptomatic *P. falciparum* malaria in a human subject, comprising:
    a) administering to the human subject two or more primary doses of a compound of Formula (I), a pharmaceutically acceptable salt thereof, or a pharmaceutical composition comprising a compound of Formula (I), wherein at least the first primary dose is administered prior to potential exposure of the subject to *P. falciparum*; and
    b) administering to the human subject one or more post-exposure dose(s) of a compound of Formula (I), a pharmaceutically acceptable salt thereof, or a pharmaceutical composition comprising a compound of Formula (I), within 1-10 days after the risk of continued exposure to *P. falciparum* has substantially ended, wherein each said post-exposure dose comprises 75 mg to about 399 mg of the compound of Formula (I),
    wherein about 75 mg to about 399 mg of said compound of Formula (I) is administered in each of said two or more primary doses,
    wherein said primary doses are administered for about 1-21 days,
    wherein the human subject is malaria-nave and Glucose-6-phosphate dehydrogenase (G6PD) normal, and
    wherein Formula (I) has the following structure,

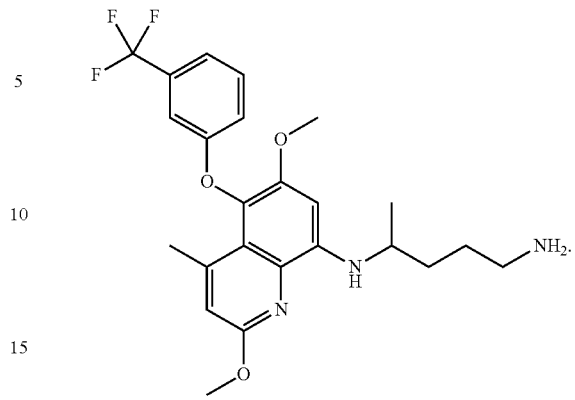

24. The method of claim 23, wherein the primary dose is administered three times.

25. The method of claim 23, wherein the administration is sufficient to produce a C min serum or plasma concentration of at least about 80 ng/mL of said compound of Formula (I) prior to potential exposure to *P. falciparum* and to substantially maintain that serum or plasma concentration throughout to *P. falciparum* in more than 50% of individuals administered the given primary doses.

26. The method of claim 23, wherein the administration is sufficient to produce a C min serum or plasma concentration of at least about 80 ng/mL of the compound of Formula (I) prior to potential exposure to *P. falciparum* and to substantially maintain that serum or plasma concentration throughout potential exposure to *P. falciparum* in 95% or more of a population of subjects administered the given primary doses.

27. The method of claim 23, wherein the human subject is an adult.

28. The method of claim 23, wherein the human subject is a child.

29. The method of claim 23, wherein the compound, the salt, or the pharmaceutical composition is administered orally or sublingually.

30. The method of claim 23, wherein the pharmaceutically acceptable salt of a compound of Formula (I) is tafenoquine succinate.

31. The method of claim 23, wherein the pharmaceutically acceptable salt of a compound of Formula (I) is a salt of tafenoquine or a salt having the following structure,

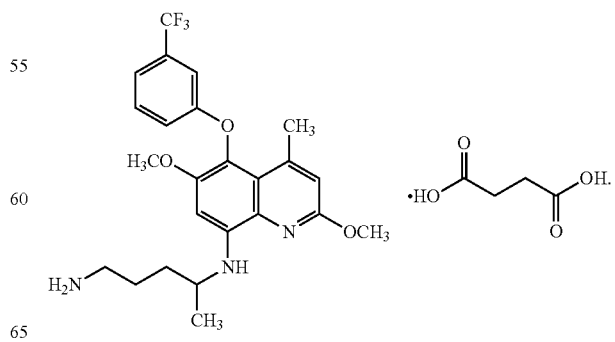

32. The method of claim 23, wherein a C min serum or plasma concentration of at least about 80 ng/mL of the compound of Formula (I) is obtained prior to potential exposure to *P. falciparum* and is substantially maintained throughout potential exposure to *P. falciparum* in the human subject.

33. A kit comprising:
  a) two or more primary doses of about 75 to about 399 mg of a compound of Formula (I), a pharmaceutically acceptable salt thereof, or a pharmaceutical composition comprising a compound of Formula (I);
  b) one or more post-exposure dose(s) of about 75 to about 399 mg of a compound of Formula (I), a pharmaceutically acceptable salt thereof, or a pharmaceutical composition comprising a compound of Formula (I); instructions for taking at least one primary dose prior to potential exposure of *P. falciparum* and taking said post-exposure dose(s) one or more times within 1-10 days after the risk of continued exposure to *P. falciparum* has substantially ended, wherein Formula (I) has the following structure,

* * * * *